(12) United States Patent
Ziobro

(10) Patent No.: US 10,664,935 B2
(45) Date of Patent: May 26, 2020

(54) METHODS AND SYSTEMS FOR REHABILITATING INJURED OPERATORS

(71) Applicant: DURO HEALTH, LLC, Portland, OR (US)

(72) Inventor: Randy T Ziobro, Portland, OR (US)

(73) Assignee: DURO HEALTH, LLC, Portland, OR (US)

( * ) Notice: Subject to any disclaimer, the term of this patent is extended or adjusted under 35 U.S.C. 154(b) by 531 days.

(21) Appl. No.: 14/875,099

(22) Filed: Oct. 5, 2015

(65) Prior Publication Data

US 2016/0098808 A1 Apr. 7, 2016

Related U.S. Application Data

(60) Provisional application No. 62/059,725, filed on Oct. 3, 2014.

(51) Int. Cl.
*G16H 50/30* (2018.01)
*G06Q 50/26* (2012.01)
(Continued)

(52) U.S. Cl.
CPC .......... *G06Q 50/26* (2013.01); *G06F 19/325* (2013.01); *G06F 19/3481* (2013.01);
(Continued)

(58) Field of Classification Search
CPC .................................................. G16H 50/30
See application file for complete search history.

(56) References Cited

U.S. PATENT DOCUMENTS

2002/0069089 A1 6/2002 Larkin et al.
2005/0108055 A1* 5/2005 Ott .................... G06F 19/3418
705/2

(Continued)

FOREIGN PATENT DOCUMENTS

WO 97-41775 A1 11/1997

OTHER PUBLICATIONS

International Search Report and Written Opinion for Application No. PCT/US2015/053881, dated Jan. 26, 2016, 10 pages.
(Continued)

*Primary Examiner* — John A Pauls
(74) *Attorney, Agent, or Firm* — Alleman Hall Creasman & Tuttle LLP

(57) ABSTRACT

The disclosed medical and rehabilitation systems and methods evaluate injured operators, medically, mentally, and occupationally. The operators are highly-trained military or law enforcement personnel that have specific tactical requirements, among other physical demands, to perform their jobs properly. The occupational evaluation of the injured operator relates to their occupational requirements and how their injuries affect their abilities to perform the tactical requirements of their jobs. The rehabilitation programs can be customized to various needs of the units, branches, or other groups to which the injured operators belong. Further, the injuries of one or more operators can be tracked and data related to operators suffering similar injuries can be used to help treat each operator and to help give commanders of the injured operators more injury data on which to base decisions about the operator and the unit or other group of operators.

19 Claims, 8 Drawing Sheets

(51) Int. Cl.
*G16H 50/20* (2018.01)
*G16H 10/60* (2018.01)
*G16H 20/30* (2018.01)
*G06F 19/00* (2018.01)

(52) U.S. Cl.
CPC ............ *G16H 10/60* (2018.01); *G16H 20/30* (2018.01); *G16H 50/20* (2018.01)

(56) References Cited

U.S. PATENT DOCUMENTS

| | | |
|---|---|---|
| 2005/0203443 A1 | 9/2005 | Salvi et al. |
| 2006/0206027 A1 | 9/2006 | Malone |
| 2006/0287879 A1 | 12/2006 | Malone |
| 2008/0133297 A1 | 6/2008 | Schmotzer |
| 2009/0281879 A1 | 11/2009 | Pandya |
| 2011/0077977 A1* | 3/2011 | Collins ............ G06F 17/30539 705/4 |
| 2012/0116548 A1 | 5/2012 | Goree et al. |
| 2016/0098808 A1 | 4/2016 | Ziobro |

OTHER PUBLICATIONS

United States Patent and Trademark Office, Office Action Issued in U.S. Appl. No. 15/419,972, dated Aug. 5, 2019, 5 pages.

\* cited by examiner

OPERATOR EVALUATION AND TREATMENT OF AN INJURY

INJURY ASSESSMENT OF OPERATOR AND TREATMENT

METHODS AND SYSTEMS FOR REHABILITATING INJURED OPERATORS

CROSS-REFERENCE TO RELATED APPLICATION

This application claims the benefit U.S. Provisional Application No. 62/059,725, filed Oct. 3, 2014 and claims foreign priority to PCT Application No. PCT/US2015/053881, filed Oct. 2, 2015, which are both hereby incorporated by reference in its entirety.

BACKGROUND

Modern warfare and law enforcement strategies require highly-trained operators. The highly-trained operators undergo extensive and expensive training and typically become the most valuable asset to their respective units. Essentially, these highly-trained operators are a very expensive, highly valuable weapons systems. Many of the highly-trained operators, like those operators who are members of the United States Special Operations Command (SOCOM), dedicate their lives to performing extremely dangerous and critical missions to protect the national security of the United States. These operators take on extraordinary risk to their personal safety and have a high risk of suffering one or more physical injuries in performing their jobs over the course of their careers.

Further, highly-trained operators are so dedicated to their careers that they ignore non-critical-failure-types of injuries because of their desire to complete a mission for their units, help a fellow operator, or meet their personal goals of fulfilling their commitment to their country. When receiving treatment for an injury, the highly-trained operators tend to push through pain and sometimes mask the pain with and without pain medication or other pain relief aids. They also tend to provide inaccurate, although genuine, subjective feedback during their medical reviews, like understating the severity of their injuries and their associated pain.

The highly-trained operators, for example the SOCOM operators, are trained in a variety of different areas, including physical training, tactical training, and psychological training. When the operators suffer a physical injury, all of their training is affected. Specifically, an injured operator may suffer a shoulder injury that requires surgery. The operator medically heals from the surgery and is returned to his unit without further assessment of his ability to meet physical training requirements of his unit or branch, perform tactical duties that are unique to the operator and/or the unit, or undergo any psychological evaluation. The operator's shoulder may appear to be medically healed, but his shoulder is not evaluated under tactical conditions, like firing his weapon(s) or performing hand-to-hand combat techniques, which leaves the operator feeling insecure about his tactical capabilities and his ability to execute missions safely and successfully and to be a productive member of his unit.

In another example, military fighter pilots, like the F-18 jet pilots, have a high incidence of neck and back injuries, some of their injuries being chronic that typically present or worsen over a long period of time. A pilot's neck injury, for example, might appear to have medically healed after a required surgery to repair an injury. However, the pilot has not yet undergone the physical demands of flying the F-18 jet, which are highly rigorous, after the surgery. Even further, oftentimes the pilots are not tested properly for the physical demands of flight before suffering the injuries to establish any kind of baseline data for the pilots' physical conditions and/or readiness to pilot their respective aircrafts.

Such pilots have unique occupational requirements of which a typical, non-pilot person suffering a similar neck injury does not because of the pilot's highly-specialized training and job duties. Specifically, piloting a fighter jet like an F-18 aircraft is known to cause chronic, degenerative neck and back injuries. The pilots are not conventionally tested under their occupational requirements to determine whether any neck or back injuries exist and that the pilots are ready to undertake the physical demands that are known to be required of such pilots. Pilots who return to an active flight status too quickly after an injury have a high risk of re-injury, further damage to the injury area, and/or may suffer development of chronic conditions or advancement of degenerative conditions.

Other highly-trained operators also have specialized occupational demands. For example, law enforcement generally has unique physical, occupational demands that might include firing or using a weapon and engaging in and resolving physical altercations. Even more specifically, highly-trained law enforcement operators, like agents in the Federal Bureau of Investigation (FBI), the Central Intelligence Agency (CIA), the National Security Agency (NSA), Pararescue troopers, the Department of Energy (DOE) special operations, specialized firefighters for the Forest Service, Special Weapons and Tactics (SWAT) teams, pilots, among others, for any of these groups undergo highly-specialized training for their jobs that includes tactical and other job-related physical and psychological training. The law enforcement highly-specialized operators have specific, physical requirements for their jobs, similar to the highly-trained military operators, to mitigate their risk of injury and to increase the likelihood that their missions are completed successfully and safely.

The military and law enforcement operators require significant training that can total $500,000 or more for SOCOM operators, for example, just to complete their initial acceptance training (sometimes referred to as the "pipeline") into the career field. The SOCOM operators undergo continued training throughout their careers, which brings the total financial investment in their training to an even higher amount. The training of the highly-trained operators is critical to the success and safety of their occupational activities, such as dangerous military missions.

Frequently, these highly-trained operators suffer physical injuries as a result of their jobs and have a period of time of being unable to perform their jobs because of the injuries. When operators are not able to do their jobs, unit commanders or the operators' other leadership have uncertainty in selecting operators to execute key missions, the operators may feel inadequate because they cannot participate in a key mission, and the operators and unit morale decreases when the unit is missing a key member and/or operators do not recover well from an injury.

When the injured highly-trained operators report a physical injury, they typically undergo medical treatment for the injury. Some of the physical injuries suffered by the highly-trained operators require several weeks to several months or even longer for a full recovery. While the injured operators are recovering, they do not typically perform the tactical and/or other physical occupational requirements of their jobs because their medical recovery requires that they stop such activities to allow the injuries to heal. Towards the end of the injured operators' healing process, medical providers analyze the injured operators to determine whether the injury is medically healed. At the time of the medical analysis of the injuries, most of the injured operators have not performed the tactical requirements that are typical or required for their jobs, which can leave the operators feeling insecure about performing the tactical activities of their jobs and potentially physically deficient after their injuries are deemed to be medically healed.

Still further, the highly-trained operators oftentimes have such intense dedication to their units, their missions, and themselves that they do not report physical injuries, they downplay the severity of an injury, they return to full duty before an injury is fully healed, and they use medication or other pain relief tools to mask their physical pain. The injured operators are not generally monitored or tracked for an injury or during the injury recovery process. A commander is typically required to make a decision on whether to rely on an operator based on whether the operators report an injury, which they may be unlikely to do, and whether they have fully recovered from the injury based on the operators' subjective, and oftentimes down-played, inaccurate feedback, and the analysis from a medical provider who evaluates the operators on typical medical standards. In the current rehabilitation programs available to operators, their commanders do not have the data necessary to determine whether the injured operators can perform their tactical duties and successfully execute a mission without a high risk of re-injuring themselves or other operators.

When highly-trained operators suffer injuries, they tend to lose confidence in their skills required to perform their job, specifically the tactical skills required to perform their jobs. The currently available medical and rehabilitation systems do not offer the injured operators the ability to measurably improve their confidence in their tactical skills after they suffer an injury and are considered medically healed. The injured operators' confidence in their physical and tactical skills oftentimes erodes after physical injuries, and their cumulative effects, which leads to some operators having a pre-mature retirement from their units, leads to reduced morale in the units, and to overall career dissatisfaction and negative public opinion of the unit, the military, and/or the government. Further, the injured operators tend to be so eager to return to their units quickly that they are willing to mask physical pain with pain medication and ignore their medical conditions that are in need of further treatment. The current medical and physical rehabilitation systems available to injured operators do not support the long-term health and well-being of the highly-trained operators, the best asset and most valuable weapons system available to any unit.

Still further, with the currently available medical and rehabilitation systems, the highly-trained operators can be returned to unrestricted duty without a comprehensive plan of care to follow-up with the operator on the injury at any future time. Instead, the operator is expected to report any future re-injury or new injury and begin the medical treatment process again, which can be daunting. Many injured operators returning to duty continue to experience physical pain or other symptoms of their injuries in performing their tactical and other occupational duties that they have not performed since before the injury. The operators experiencing continued physical pain from their injuries may rely on pain medication to mask the physical pain of the injuries without realizing that their injuries need further medical treatment or without wanting to seek the further medical treatment. Masking physical pain with pain medication is dangerous to the operators' health and increases the risk of re-injury and failed missions.

By releasing the operators back to full duty status based on their subjective feedback and a medical evaluation alone, the operators' commanders do not have any data to assess the operator's tactical abilities and capacities, improve unit safety procedures, assess budget requirements, develop new training, determine personnel needs for mission planning and other reasons, succession planning, etc. The Commanders also struggle to hold the returning operators responsible for any continuing medical treatment that might be recommended or required to continue the operators' injury recovery process and/or to help prevent re-injury because the Commanders do not have injury benchmarks, metrics or any such data to do so.

If a commander has an injured operator that needs future or ongoing medical treatment, the current medical and rehabilitation systems do not inform the commander of the recommended medical treatment and do not lay out a plan for the commander to supervise the operator in undergoing the medical treatment. Current medical and rehabilitation systems do not engage the commander in the future medical treatment of an injured operator after the operator is returned to full duty status or provide the commander with data driven tactical capacity assessment baselines to monitor the operator after returning to full duty.

Because of the government's and law enforcement's responsibility to their highly-trained operators, such as the SOCOM operators, an injured operator's injury maintenance system is needed to evaluate and treat the injured operators with a customized treatment plan. The art could benefit from an injury maintenance system that provides to the injured operator a future plan of care and optionally provides to the operator's commander an injury report that includes both the medical and occupational evaluation and treatment. Still further, the art could benefit from an injury tracking system.

DETAILED DESCRIPTION

Figure 1:
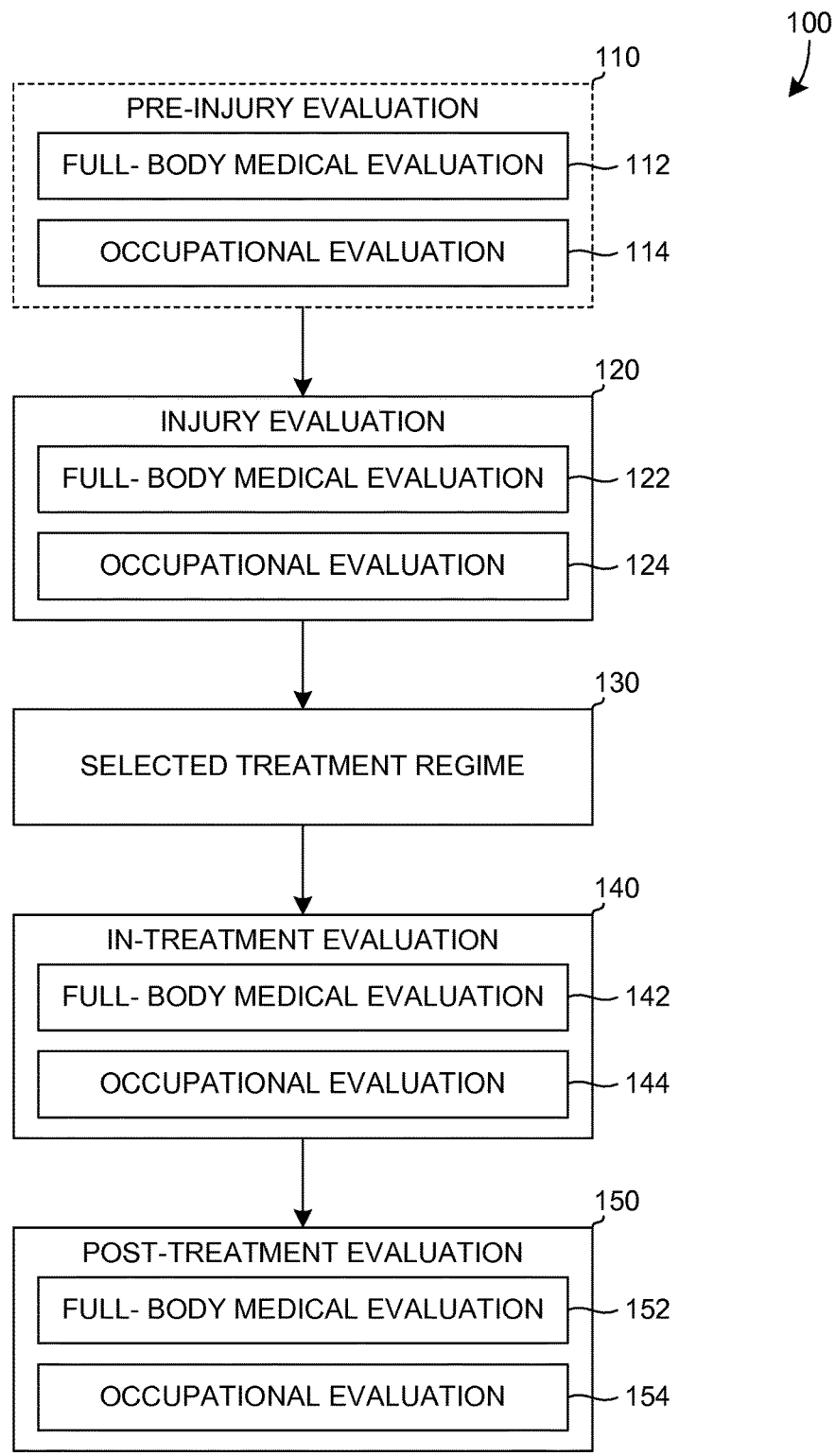
FIG. 1 is an example evaluation and treatment process of an operator according to an embodiment of the invention.

The disclosed methods and systems of rehabilitating and evaluating injured operators serve as an operator evaluation, maintenance, and rehabilitation system. The highly-trained operators are the most valuable assets of any military unit or law enforcement team. The highly-trained operators are often required to perform dangerous activities as part of their regular jobs. Providing the operators with the highest quality, customized medical and occupational treatment at any and all times during their careers, pre-injury, post-injury, or both, helps to meet the duties owed to these operators to take care of them. The disclosed rehabilitation methods and systems provide an operator maintenance system that helps evaluate, treat, and create a plan of care for operators both medically and in all aspects that are important to the operators' occupations.

The disclosed methods and systems provide resiliency to each operator by assisting them to have a full-length career and a high quality of life that significantly improves their chances of being free of physical limitations and pain in retirement or mitigates the potential risk of such chronic medical conditions. A full-length career for highly-trained operators is becoming increasingly critical. An experienced leadership void in special operations is growing at least in part due to musculoskeletal injuries, among other injuries, which increases the number of operators choosing to separate from their respective units before retirement or a full-length career instead of staying in the military to achieve a leadership position.

The disclosed rehabilitation methods and systems are designed for all types of highly-trained operators having occupational requirements that extend beyond normal physical and/or mental activity. For example, an operator can be a member of the military generally or, more specifically, a SOCOM member like a Navy Seal, an Army Special Operations Forces member, or a military fighter jet pilot. Also, the operators could be members of law enforcement, like a member of the FBI, CIA, DOE special operations unit, NSA, SWAT teams, or the like. Still further, the operators can include members of elite teams like Pararescue members and firefighters who fight large forest fires.

The highly-trained operators undergo extensive, expensive, lengthy training and education to qualify to perform their jobs. Their jobs require intense physical demands. The physical, occupational demands require that the operators are in peak physical condition, especially after recovering from an injury, to successfully and safely perform their jobs. An operator can be any person having specialized, physical demands in their occupation, whether it is military or law enforcement related or in the private sector industry, manufacturing or otherwise.

The risk of physical injury to the highly-trained operators is very high. The injuries include both chronic and acute injuries and both physical and mental injuries. Oftentimes, physical injuries are related to mental injuries and the operators can suffer from more than one type of injury at the same time. For example, an operator could suffer a labral tear in his shoulder during a mission. The operator undergoes surgery to repair his labrum and extensive ongoing physical therapy is required to medically rehabilitate his shoulder.

In another example, an operator suffers from a degenerative spine disorder, like a bulging disk, which is common among fighter pilots. Still further, an operator could suffer many injuries during a mission, both physical injuries like broken bones and torn ligaments, and mental injuries like post-traumatic stress disorder (PTSD). In the disclosed rehabilitation methods and systems, each of these injuries is evaluated, treated, and followed-up from both a medical and an occupational perspective. In the cases where the operators are military members or law enforcement, the occupational part of the analysis of the operators' condition can include evaluating, treating, and follow-up with the operators from a tactical perspective.

The disclosed rehabilitation methods and systems can also be used with operators that are in the private sector, like in a corporate, industrial, manufacturing or other environment in which the occupation requires specialized physical demands. For example, a foreman of a construction crew has an injured employee. The injured employee goes through medical treatment for his or her injury. At some point, the medical providers decide that the injured employee is medically healed and ready to return to work. At that time, the injured employees can be evaluated both medically and for any physical, occupational requirements for their job.

FIG. 1 illustrates an example evaluation and treatment process 100 of an operator according to an embodiment of the invention. As part of the process 100, the operator can undergo a pre-injury evaluation 110 that includes a full-body medical evaluation 112 and an occupational evaluation 114. The pre-injury evaluation 110 can be performed on operators at regular predetermined intervals to establish baseline medical and occupational fitness levels for each operator.

Upon injury, the operator undergoes an injury evaluation 120 that includes a full-body medical evaluation 122 and an occupational evaluation 124. The medical evaluation 122 establishes the extent of physical, and optionally the mental, injury to the operator. The occupational evaluation 124 of the operator assesses the impact of the operator's injury on his or her occupational performance.

Once the operator has been evaluated for medical and occupational fitness, the operator can begin a treatment regime 130 selected, or developed, based on the assessed operator fitness.

As the operator undergoes treatment, the operator can be regularly assessed 140 for medical and occupational fitness to track progress, and optionally the efficacy, of the selected treatment regime 140. A fully-body medical evaluation 142 and an occupational evaluation 144 can be used to assess the medical and occupational fitness of the operator during treatment.

After treatment is complete and the operator is returned to occupational status, he or she can continue to undergo both physical and occupational fitness evaluation 150 to monitor the injury and overall operator fitness going forward. The post-treatment evaluation 150 can include a full-body medical evaluation 152 and occupation evaluation 154.

The Operator's Full-Body Medical Evaluation and Assessment

The medical portion of the evaluation, treatment, and follow-up can include a full-body musculoskeletal medical evaluation of the operator after the injury occurs and, optionally, before the operator suffers the injury to set baseline musculoskeletal data for the operator in the event they ever suffer an injury. Comparatively, the typical medical evaluation that occurs when the injured operator's healing appears to be complete includes a medical evaluation of the injured body part, not the operator's entire body.

The full-body medical evaluation(s) can be performed on the operators at any time during their careers. In some examples, the operators are medically evaluated upon entry into their occupations, and in the military examples into their respective special operations units. For these entry-type medical evaluations, the operators are typically evaluated for baseline medical data along with trying to identify any physical or medical areas that may be weak or could use conditioning and improvement. Further, the operators can be periodically medically evaluated throughout their tenure in their occupations as a monitoring and tracking type of medical evaluations. Periodic evaluations can be done on a regular schedule or can be performed, as needed. The fully-body medical evaluations performed at the entry to or periodically throughout the tenure of the operators' relationships with their occupations are considered a "pre-injury" type of medical evaluation herein. Pre-injury means that the operators have not suffered a known or acute injury.

The full-body medical evaluation(s) can also be performed at the time or shortly after the time an operator suffers an injury or discovers an injury, whether the injury is acute or chronic, and are considered a "post-injury" type of medical evaluation in this context. As part of the medical evaluation of the operators' injuries, the operators undergo a full-body medical evaluation. The full-body medical evaluation differs from a typical medical evaluation in that it assesses the operators' entire bodies using both subjective and objective analysis. Oftentimes, conventional medical evaluations focus only on the injured body part and do not consider the remainder of the operators' bodies during the medical evaluation. As discussed further below, multiple full-body medical evaluations can be performed on the operators after an injury occurs.

The post-injury full-body medical evaluation(s) for an injured operator can be compared to known or conventional full-body medical data for other operators with similar occupational requirements to the injured operator. Additionally and/or alternatively, the post-injury full-body medical evaluation(s) can be compared to the operator's pre-injury full-body medical evaluation(s) if any exist.

The full-body medical evaluations of the operators can be customizable to any level of granularity and/or at multiple levels of granularity within any organization. For example, the military special operations operators can be evaluated and/or compared to other operators in their military branch, their unit, their squadron, and to other special operations operators in related units or even branches of the military who have similar occupational requirements to the injured operator. In another example, operators can be compared to other operators with similar populaces, ages of injury types, origin of injuries types of injuries, location of injuries (whether the injuries occurred when the operator was deployed v. non-deployed), surgical status of the injuries (whether the injury required a surgical procedure or a surgical procedure is recommended), and the like.

Still further, the injured operators can also be compared to various trending metrics, such as outcomes of similar injuries suffered by other operators and other operators' rates of completing a treatment and/or rehabilitation program (e.g., if operators are likely to fail to complete some portion of the treatment or rehabilitation). Cost analysis for similar injuries among operators with similar occupational requirements can be performed along with other financial analysis like comparing multiple medical providers' treatment plans or billing practices for operators with similar injuries and similar occupational requirements. The injury trending metrics is described further below.

The medical evaluation can be or can also include a physician-based injury evaluation, which is a medical assessment of the injured operator by a physician or other medical providers or group of providers. The physician-based injury evaluation can include objective physical examinations, such as orthopedic and neurological tests, objective observations by the medical providers, and subjective assessments by the medical providers. In some examples, specific injuries like back, neck, and knee injuries can be medically evaluated by using various equipment to evaluate the musculoskeletal and other medical issues associated with the operators' injuries. The testing equipment collects the injury data in a hard data format, in some examples, or can collect the injury data in a software format for electronic storage and analysis.

For example, various medical equipment, like the MedX™ technology available from MedX™ Corporation in Ocala, Fla., can generate specific data points relevant to evaluating the injuries of operators. Specifically, for operators suffering from a back or neck injury, the injury strengthening and/or evaluation equipment, calculates data for specific aspects of the operators' physical condition like range of motion, strength in various positions, and the like. Alternative injury strengthening and/or evaluation equipment can be used that can quantify or otherwise evaluate the medical condition of the injured operators. Further, this medical evaluation process can be performed by one or more medical providers who evaluate and test the injured operator for specific medical conditions and then assigns various values to the medical conditions that correspond with the results. As mentioned above, the injury strengthening and/or evaluation equipment can be linked to software and additionally or alternatively medical providers can input the operators' full-body medical evaluations into the software.

Oftentimes, the treating medical team for the injured operators has determined that the operator has completed medical recovery and is able to return to full duty status. However, the treating medical teams often look only narrowly at the injury and the specific, injured body part's function and compare it to standard medical protocols for determining that a patient is considered to be healed. However, following a standard medical protocol is not going to uncover medical and/or tactical deficiencies that the injured operators may face in the future, especially in returning to full combat mission ready duty status in the SOCOM operators for example.

The disclosed medical and rehabilitation systems and methods can provide an extensive, full-body medical evaluation, in addition to the medical evaluation of the injured body part. The extensive, full-body medical evaluation can be used in determining whether the injured operator is ready to return to full duty status, in developing a future plan of care of the injured operator, and in determining other physical areas that could have been affected by the injury or could generally use improved strength and conditioning work.

For example, the medical evaluation includes a full-body musculoskeletal evaluation by one or more physicians or other medical providers along with a complete medical physical capacity assessment that evaluates the operators' strength, endurance, and range of motion over their full body, not just the injured body part. Further, the injured operator can, in some examples, undergo a soft tissue assessment and treatment by a soft tissue expert medical provider to assess and treat the operator's muscles, nerves, tendons, and the like. An example soft tissue assessment includes evaluating the operator's rhomboid, infraspinatus, anterior deltoid, triceps/axillary nerve at quadrangular space, brachiloradialis, quadriceps tendon, bilateral soleus, etc.

Some of the medical evaluation areas include physical capacity assessments that evaluate the operators' physical condition for one or more of range of motion, strength, strength curve shape abnormality, stored energy and fiber type in a variety of areas like lumbar, cervical, thoracic, knee flexion, knee extension, comparison of knees in flexion and extension, torso rotation, cervical rotation, and any other desired area. Further, the medical evaluation areas can also include range of motion testing for one or more of the operators' joints, like the shoulder(s), elbow(s), wrist(s), hip(s), knee(s), and ankle(s).

The operator's upper extremity joints, which include the operator's shoulders, elbows, and wrists, can be tested on flexion, extension, abduction, internal rotational at various degrees of abduction, external rotation at various degrees of abduction, supination, pronation, radial deviation, ulnar deviation, and the like. The operator's upper extremity joints can also be medically evaluated in additional or alternative manners like in grip, pinch, and full-arm performance types of test. For example, the grip tests might evaluate an operator's upper extremity, both sides, in a handle or brief case test, a cylinder test, a fist/bar/club test, a spherical test with the operator's whole hand holding an object like a baseball, and a trigger test with a weapon, for example.

The pinch tests can evaluate an operator's upper extremity, both sides, in a three-fingered chuck with a pencil or other object, a lateral or key test, and a tip or fishing line test, among others. Still further, the full-arm performance tests might include a push-up with the operator's arms shoulder-width apart, a push-up with the operator's arms outside of shoulder width position, an over-hand pull-up in a narrow hand position, an overhand pull-up in a wide hand position, an under-hand pull-up in a narrow hand position, and an under-hand pull-up in a wide hand position.

Even further, the medical evaluation can include lower extremity range of motion testing for the operator's hips, knees, and ankles. The lower extremity range of motion testing includes flexion, extension, abduction with the operator in a supine position, external rotation with the knee at 90° flexion with the operator in a prone position, internal rotation with the knee at 90° flexion with the operator in a prone position, inversion with the operator in a supine position, and eversion with the operator in a supine position, for example.

The operator's gait can also be tested during the medical evaluation. The gait tests include a walking test with the operator moving at approximately 3.0 miles per hour (mph), a running test with the operator moving at approximately 8.0 mph, and a sprinting test with the operator moving at approximately 12.0 mph. Other gait tests can be used. Further, the operator's cardiovascular endurance can be tested on a treadmill or bike, for example.

During any one or all of the medical evaluations, the medical providers can observe the technique and flexibility of the operator along with the physical capacity, range of motion, gait, and cardiovascular endurance. Any medical and/or physical aspect of the operator's performance is evaluated during the medical assessments.

Some of the medical evaluations can include medically testing the operator's joints for tactical physical capacity. Tactical physical capacity is a particular action, movement, position, or other physical demand that is required of the operators to successfully perform their jobs. For example, the tactical physical capacity includes leg length measurements taken supine to sit, a squat (bilateral LE or lower extremities ischial tuberosities that reach calcaneus, B US raised to 90° performance), feet flat descend symmetrical, feet flat rise symmetrical, heels off the ground descend symmetrical, raised surface 18 inch test (unilateral LE lower extremities, to full knee extension, B UE (upper extremities), lowered with B elbow flexed to 90° performance with the operator's full foot on the raised surface and again with the operator's ball of foot on the raise surface, the balance test (unilateral LE lower extremity B UE raised to 90° abduction performance) held for about five seconds or another length of time with the operator's eyes open and knee straight, with the operator's eyes closed and kneed straight, with the operator's eyes open and knee flexed to 15°, and with the operator's eyes closed and knee flexed to 15°.

The medical assessment of the operators further includes a strength evaluation that tests the strength of one or more physical aspect of the operators, for example. A strength evaluation includes both upper and lower extremity tests. The upper extremity strength tests include a unilateral lateral raise, bilateral overhead press, isometric flexion, isometric extension, isometric abduction, isometric internal rotation at 0° abduction, isometric external rotation at 0° abduction, isometric supination with the operator's elbow at 90°, isometric pronation with the operator's elbow at 90°, unilateral supination with the operator's elbow at 90°, unilateral pronation with the operator's elbow at 90°, unilateral flexion with the operator's elbow at 90°, unilateral extension with the operator's elbow at 90°, and grip strength with the operator's elbow at 90°.

The operator's lower extremity strength can also be tested. The lower extremity strength tests include flexion, isometric extension, isometric abduction with the operator in a side-lying position, isometric external rotation with the operator's knee flexing 90° with the operator in a prone position, isometric inversion with the operator in a supine position, and isometric eversion with the operator in a supine position.

Other range of motion, strength, gait, and cardiovascular tests on any of the joints can also be included. Pain, crepitis, popping, tightness, and/or other physical indicators of injury observed by the medical provider when evaluating the operator throughout the full-body medical tests can be noted and included in the medical assessment.

The medical providers can choose to evaluate the operator in any one or more of the above-described medical evaluations and assessments. In some examples of the disclosed rehabilitation methods and systems, the operator undergoes some combination of tests, evaluations, and assessments to give the medical provider enough data on the physical condition of the operator's full body. In some cases, one or more of the medical assessments can be performed multiple times with the operator.

The full-body medical evaluation is customized to the operator, in some examples. The customization can occur in a variety of ways, such as customizing based on one or more of the following: type of injury, operator's unit, severity of injury, tactical requirements for operator, and the like. Again referring to the level of granular customization discussed above, the full-body medical evaluation can even be customized based on the injured operators past medical history, including but not limited to their past injury history, propensity for injury, whether the operators completed the recommended treatment and/or maintenance program and the like.

Each way to customize the full-body medical evaluation can be done based on different criteria. For example, a SOCOM operator suffers a combat-related shoulder injury. This SOCOM operator is medically evaluated based on other SOCOM operators who suffered similar shoulder injuries, other operators with the same unit that suffered similar injuries, the operator's past shoulder injuries if any exist, and any special tactical requirements for this particular operator's position. The special tactical requirements could be from other operators in SOCOM or elsewhere that have similar tactical requirements to the injured operator. The medical evaluation can be customized in any desired way.

The medical portion of evaluating the injured operator can occur immediately or within a short time after the injury occurs or could be performed after a period of time has elapsed post-injury. In some examples, before the operator then commences the disclosed rehabilitation program the operator must be unable to return to his occupational duties for a period of at least four months or any other determined period of time. The operators can be selected by their commanders or their leadership to participate in the program for any reason, including the type or severity of the injury suffered by the operator, the length of their expected time away from duty, the manner in which the recovery and/or treatment has progressed, the previous success of other operators suffering similar injuries that participated in the program, the type of occupational demands required of the operator, and any other suitable reason. Alternatively, the operators can opt to participate in the disclosed medical and rehabilitation systems and methods themselves for any reason.

The Operator's Occupational Evaluation and Assessment

The occupational portion of the evaluation, treatment, and follow-up of an operator can include a variety of tests and evaluations. The occupational portion can include tactical evaluations, for example, which is any unique feature(s) of or specialty skill(s) required by the operator's occupation. In the examples with the operators being industrial or manufacturing workers, the occupational evaluation could also include testing for fine motor skills in machining or physical requirements for operating heavy machinery, etc. Generally, the example occupational evaluations discussed herein are focused on military, tactical evaluations, but these are examples, and the disclosed occupational evaluations can include any physical or mental requirement of the operator's occupation and can include operators in the private, civilian sector as well as those operators in the armed forces and law enforcement.

With the military SOCOM members, for example, the operators are tested and evaluated based on situational, tactical skills. The tactical skills simulate tactical situations under and through which the operator's injury is evaluated. The tactical situations could be the requirements of the operator's unit, the operator's branch physical training, the operator's job in the unit, the operator's status with respect to a mission, or the like. The evaluated tactical situations are customized to the operators' specific and unique tactical requirements for successfully performing their jobs. Some are unit/occupation specific while others can be operator-specific. The tactical evaluations can be customizable based on any aspect about the operator, the operator's occupation, a mission requirement, and any other criteria, including operators' strengths and weaknesses, in some examples.

Like with the full-body medical evaluations, the occupational, and in an specific example the tactical evaluations, can be performed both before and after an operator suffers an injury. The pre-injury occupational data can be used as a baseline for later comparison if the operator suffers an injury. Ongoing occupational evaluations can also be used for comparison to later post-injury data and can additionally be used for monitoring the operators for performance and chronic onset types of injuries.

The occupational evaluations can include both objective and subjective assessments, in some examples. Objective occupational assessments can be performance based, such as target tactical shooting and other hard data results of specific tactical activities or activities that simulate a tactical maneuver. Subjective occupational assessments can be an opinion of an observer about the manner in which the operator completes a particular activity in the tactical assessment. Some operators exceed expectations in one or more tactical assessments, even when they are suffering from an injury so the addition of subjective tactical assessments can provide another angle on the operators' injuries.

The tactical tests for military operators can include any one or more of the following: tactical physical capacity assessment, tactical assessments, and branch- or unit-specific physical training tests. The tactical physical capacity assessments include evaluating the operator through a combat physical capacity assessment, an obstacle course, a grip test, a buddy carry, a parachute landing, and other tactical assessments. The tactical assessments include tests like a land-based free fall, land-based assessment at a drop zone, a wind tunnel free-fall, tactical shooting and/or target practice, open-water swimming, open water combat techniques, pool swim, hand-to-hand combat, and the like. Other tactical assessments include military free fall, SCUBA-dive swim, combat driving, all-terrain vehicle (ATV) or dirt bike driving, fast roping, etc. The branch or unit specific physical training tests are physical requirements for each branch, unit, or other occupational group and are oftentimes regularly scheduled for each member of the occupational group. For example, the Marine Corps has specific physical training requirements on various physical activities like distance running, sprints, swimming, strength training, etc. and the injured operators can be evaluated on these standards post-injury.

For a free-fall at the drop zone assessment, which is a test of how well the operators can withstand a free fall to a drop zone target are jumping out of an aircraft (or other starting place), the operators are evaluated on their pre-flight rig inspection, whether they can achieve an "arch and shoot" position, whether they can complete a parachute landing fall, whether they can perform "practice rip cord pulls" in prone position, whether they can perform "cutaway procedures in prone position," when the operator can assemble and apply a rig to himself, whether the operator can enter the aircraft, whether the operator can maintain an "in flight posture," whether the operator can achieve a "ramp posture," and whether the operator can exit the aircraft.

In a land-based, basic free fall, which is a test of how well the operators can withstand a free fall when they are jumping from high ground like a cliff, the operator is evaluated to see if he can achieve a freefall position, check left, check right, check altimeter, practice rip cord pull, wave off, complete opening procedures, conduct post-opening procedures, unstow toggles, fly the parachute, flare the parachute at pre-landing, land, disassemble his weapon, demonstrate combat mission ready position, and disengage from the rig. A similar assessment of the operator can be done with the land checks at the drop zone assessment.

A free fall at the wind tunnel assessment includes evaluating the operator on entering a tunnel used by parachuters/skydivers for practicing free falls, initiating a free fall position, maintaining proper free fall position, performing "practice rip cord pull" procedures, exiting the tunnel, and the total time in the tunnel. There can also be a timed wind tunnel performance section where the operator is required to perform a predetermined number of freefall maneuvers in a set period of time. The results of the timed section could be used to compare with previously gathered baseline, pre-injury data if it exists.

The weapons assessment could include evaluating the operator in a low crawl with the weapon, firing the weapon after the low crawl, and firing a pistol from a hip position. In the examples in which the injury is directly affected by a particular tactical skill, the operator can be evaluated more extensively or with greater specificity in the shoulder-specific tactical activities. For example, a shoulder injury is known to be sensitive to the force applied by the butt of the M16 rifle when it is fired. Operators suffering from shoulder injuries might need additional or repeated evaluation for the types of tactical skills that are known to be more difficult with specific weakened physical areas, like an operator's injured shoulder when the operator needs to accurately fire an M16 rifle. The additional or repeated evaluation can be customized to the operator based on any number of factors like those tactical requirements that are specific to the operators' injuries.

The weapons assessment also includes evaluating the operator in assembling the operators' weapons in preparation for the testing range, assembling and applying their uniform and personal "kit" in preparation for testing range (e.g., equipment or other gear that is carried on the operator), and evaluating precursor exercises, such as kettle bell exercises. The operators can further be tested on their weapons range course entry, like in retaining four loaded rifle magazines at designated stations, demonstrating correction for weapon malfunction throughout the course, retaining 25 pound gear bag and proceeding to the course, and loading and charging multiple weapons systems.

The weapons assessment can also include performing certain tasks on command, which are tasks that the operator is required to perform after receiving a instruction and sometimes required to person in determined response time, such as achieving cover in a standing position, firing two rounds, moving to the next position, achieving cover in a prone position, firing three rounds, achieving cover in a kneeling position, firing one or more rounds of the weapons with the operator's weak or non-dominant hand, injured, or non-dominant hand, achieving cover in a sitting position, reloading the weapons, achieving cover behind tires in a "weak hand prone" position, switching cover position, performing low crawling with weapons, and secure the weapons and exit the course. The weapons assessment can also include a timed, scenario course where the operators are given an objective for their timed course portion of the assessment and they can self-determine shooting positions while engaging multiple targets to achieve their objective before exiting the course. The time from course entrance to course exit is then recorded and could be compared to baseline, pre-injury data, if it exists.

The hand-to-hand combat assessment includes evaluating the operator in movements and transitions, like sliding forward and backwards, shuffling forwards and backwards, and pivoting that are typically encountered during hand-to-hand combat. Further, the operators are evaluated in whether they are successful in a breakfall from a seated, squatting, and standing position or a push. A breakfall is when the operators are asked to break their falls from various positions, i.e., the operator is in the particular position and falls, loses balance, or is pushed over. The breakfalls can be from various directions like backwards and side. Still further, the operators are evaluated in their breakfall skills based on their ability to achieve a proper position, their ability to post to lift and swing their body, their ability to move their swinging leg behind their posted arm, and their ability to achieve a standing position after the kick is completed.

The hand-to-hand combat skills of the operator are further tested in their kicking skills that include evaluating their ability to touch their knee and foot to a target with proper mechanics, their ability to knee or kick a target with 50%, 75%, and 100% power, among other skills. The operator's indirect kicks, like their angled knee kick and their round kick can also be tested.

Further, the operator's tactical skills are tested on direct strikes, such as jabs, cross strikes, indirect strikes like hammer-fist strike, blocking, and the like. The operator's ability to push a target with proper mechanics is evaluated along with various skills striking a target at 50%, 75%, and 100% power. Further, the operator's ability to perform various drills, like a "weather the storm" drill, can be evaluated. For example, the weather the storm drill includes evaluating the operator on basic blocking and covering movements, blocking a strike to the operator's head and body, etc., all performed at selected power levels like 25% power and 50% power.

Still further, the operators are evaluated on safe zone techniques in a variety of safe zones, which are hand-to-hand combat techniques to protect the operators' bodies. For example, the operator's safe zone techniques are evaluated to determine if the operator can hold the safe zone at various power levels of resistance being applied, such as 25%, 50%, 75%, and 100%. The operators can also be evaluated on their tactical skills related to mount escapes like trap and roll techniques, for example. The trap and roll techniques include evaluating the operators on whether they can bridge to a top position without a partner, complete the trap and roll with no resistance, complete the trap and roll with 50% resistance, and complete the trap and roll with 75% resistance, or any other applied resistance.

The operators are also evaluated on their guard pass skills, which are hand-to-hand combat techniques used to escape dangerous physical situations such as their elbow escapes at various resistance levels, such as 25%, 50%, 75%, and 100%. Additionally, the operators are evaluated no their projector, infantry, anti-tank (PIAT) drills that include movement, punching, and kicking drills. The PIAT drills can, more specifically, include padwork to evaluate the operator's striking and kicking techniques and footwork, striking kicking, and kneeing techniques. Further, the PIAT drill evaluation includes evaluating the operator on the clink/takedown drills like clinching safe zone control, movement, takedown, standing up from ground grappling, mount escape, guard pass, and stand-up. Still further, the operators are evaluated on their final sign-off skills like martial arts techniques, for example.

The tactical evaluation also includes a combat swim assessment in some examples. The combat swim can be performed with fins, mask, and snorkel or otherwise. The operators are evaluated on whether they can apply their fins, mask, and snorkel; carry a full tank for a particular distance, like 20 yards, for example; and perform various swim methods like lead arm, trail arm techniques and a combat stroke, for a particular distance like 750 meters.

Further, the operators are evaluated in an open-water swim with or without full dive gear. The open-water swim can evaluate the operators in the following various areas, among others: $O_2$ tank carry for a desired distance; ability to assemble and apply open-swim gear, including all dive gear; perform proper water entry from boat; perform equipment surface checks; descend below water surface; re-perform equipment surface checks; descend various distances below water surface, such as 10 feet, 20 feet, and 30 feet while optionally testing the operators' abilities to perform Valsalva or other breathing tests or techniques at each respective dive depth; disengage swim and optionally dive gear; achieve swim ready position with compass board; swim a desired distance like 500 meters with a compass board to a particular target; perform a tactical peak of target and read the target; successfully exit the water; demonstrate CMR (Combat Mission Ready) position for land assault post-swim; and remove swim and dive equipment.

The operators are also tested in a pool swim, with or without full dive gear. The pool swim can be performed prior to the open-water swim, in some examples. The pool swim evaluation can include testing the operators in their abilities to don dive equipment; carry an $O_2$ tank; enter the pool;

conduct emergency procedures like a second stage regulator or other breathing device retrieval, buddy breathing, ditch and don, mask clearance, and ensuring neutral buoyancy. Further, the pool swim evaluates the operators in their abilities to swim a particular length like 25 meters, for example, with a compass board; perform a 30 second tank tread with a 15 pound or other sized weight belt; exit the pool with all gear; and remove equipment. Each of the operator's pool swim evaluations can be assessed either with or without gear. Each operator's swimming technique can also be assessed by pool-side stroke analysis.

Still further, the operators are evaluated on their abilities throughout a tactically-designed obstacle course. The operators can be required to perform the obstacle course with and without gear or both. The obstacle course can include assessing the operators' abilities on running on a flat surface; running on an uneven surface; climbing technique over an obstacle wall; climbing technique to descend obstacle wall; ability to jump onto a raised surface; ability to perform a low jump over a raised surface that is relatively low from the ground, such as being 2.5 feet above ground by using a vault or jump technique; ability to safely balance while maneuvering a narrow surface; ability to engage a rope; ability to ascend a rope of a particular height like 14 feet; ability to descend a rope of a particular height like 14 feet; ability to disengage a rope and resume the obstacle course; ability to complete an "up and over" bar of a particular height like 8 feet high; ability to complete a combination obstacle of hand-over-pipes skills, a log walk, and a high roll-over log; ability to complete a medium roll-over log of a height, such as 5.5 feet; and ability to successfully navigate vault logs, such as vault logs that are 4.5 feet in height.

Still further, the operators' combat driving is evaluated, in some examples. The combat driving assessment includes skills like being able to start the vehicle; performing turning techniques at a normal speed and at a high rate of speed; being able to maneuver the vehicle using escape techniques during a simulated attack; firing one or more weapons while driving the vehicle; maneuvering the vehicle over a raised surface and/or an uneven surface and/or around an object in the driving pathway; and disengaging the vehicle and demonstrating combat ready position. Specifically, the combat vehicles on which the operators are tested can include all-terrain vehicles and dirt bikes, for example.

During the tactical skills evaluation, the operators are also tested on their fast roping skills, which is a technique for descending a rope quickly, such as assembling and applying their personal gear; demonstrating proper ready position; engaging the rope, descending the rope; performing a dynamic brake and seated "L" position while engaging the rope; disengaging the rope, and demonstrating combat ready position after disengaging the rope.

The operators are also evaluated on tactical maneuvers in some examples, such as running on a wet or muddy surface; performing a "caving ladder" climb with a weight added, such as 35 pounds; executing a buddy drag and a buddy carry for a particular distance such as 50 yards; demonstrating the ability to low crawl for a distance like 50 yards; demonstrating the ability to ascend a rope for a height like 20 feet; performing a rope exchange with a hanging handle; and descending a rope from a height like 20 feet.

Even further, the military operators each have respective branch physical training (PT) requirements and may also have unit or other group requirements. For example, air combat controllers, special operations weather team (SOW-T), and common remotely operated weather station (CROW) operators in the United States Air Force have specific unit PT requirements in addition to their Air Force branch PT requirements. Similarly, the rangers and Green Berets in the Army and the Seals and Special Warfare operators in the Navy also have unit-specific along with branch-specific PT requirements. The Marine Corps itself has specific requirements for their critical skills operators in addition to the Navy branch PT requirements.

The PT requirements, whether unit-specific, branch-specific, mission-specific or otherwise, can include chin-ups, sit-ups push-ups, and running. For example, the Air Force requires its combat controller operators to be able to perform 20 pull-ups in two minutes from a "dead," under-hand hang, with their arms shoulder width apart and reaching their chins fully over the chin-up bar with each pull-up performed. Similarly, the Air Force combat controllers are required to be able to perform 100 sit-ups in four minutes with their backs flat, hand on their heads, head off the ground, knees bent to 90°, feet held down, all while raising their backs to vertical with each sit-up performed.

The Air Force combat controllers are required to be able to perform 60 push-ups in two minutes with their hands slightly wider than shoulder width, fingers forward, and elbows extended, lowering to their upper arms are parallel to the floor with their elbows bent to 90°. The Air Force combat controllers are also required to perform a 3-mile run within a designated period of time, such as 23 minutes, for example and perform a 1500 meter swim with mask and goggles, fins, and optionally a snorkel in any swim stroke technique within a particular time period. The above example PT tests may change at any time for any group of operators. If the PT tests change for the injured operator's group, the injury assessments, both full-body medical and occupational, may correspondingly change to reflect the new standards required of the operator.

Any of the above-discussed tactical evaluations can be performed either with or without oxygen and with or without the operator's ruck sack and/or other gear. A rating is assigned to any one or more of the tactical skills or other occupational skills that are evaluated. The ratings are typically quantified on a scale that demonstrates the operator's skill level in all evaluated skills. The individual ratings can be compiled into an overall rating, which is also quantified. The individual and the overall tactical ratings can be matched with a scaled-description, such as a scale of unsatisfactory, satisfactory, excellent, or outstanding.

The operators can optionally be tactically evaluated for an add-on tactical skill. An add-on tactical skill is one that is somehow specific to the operator and might include a skill that is traditionally weak with the type of injury suffered by the operator; a skill required for the operator's specific unit or for a specific mission for which the operator has been selected; or any other skill unique to the operator's occupation. Any number of add-on tactical skills can be included in the tactical evaluation of the operator.

Figure 2:
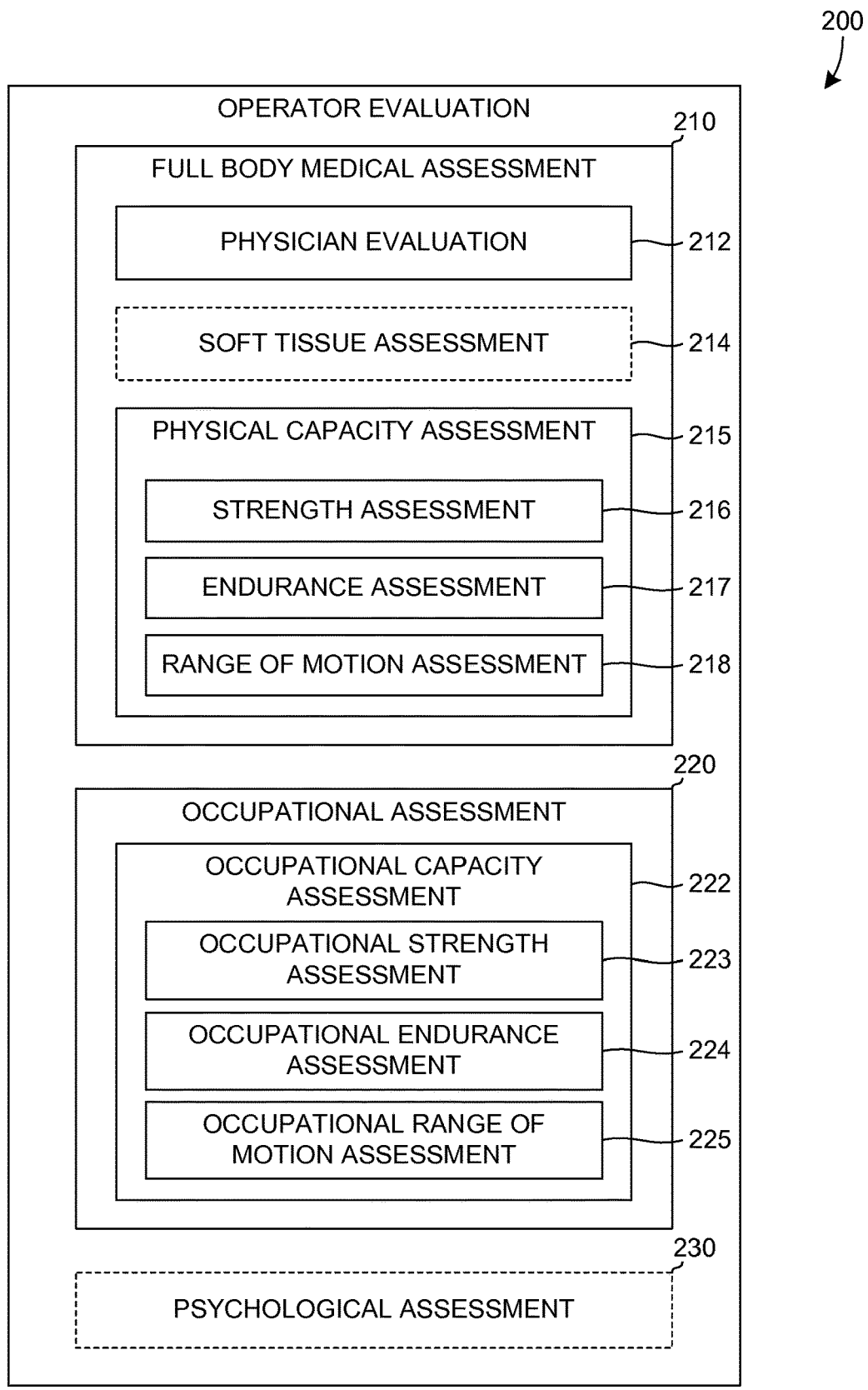
FIG. 2 is an example operator evaluation according to an embodiment of the invention.

FIG. 2 is an example operator evaluation 200 according to an embodiment of the invention. The operator evaluation 200 can include a full-body medical assessment 210, and an occupational assessment 220 and, optionally, a psychological assessment 230. The operator evaluation 200 can be performed on an operator as part of a regularly scheduled screening, which establishes a baseline fitness level for the operator and/or can be performed on an injured operator.

The full-body medical assessment 210 can include a physician evaluation 212, an optional soft tissue assessment 214 and a physical capacity assessment 215. The physician assessment 210 can be performed by one or more physicians who can both objectively and subjectively evaluate the physical health of the operator. The physical capacity assessment 215 can include a strength 216, an endurance 217 and/or a range of motion 218 assessment. These assessments, 216, 217 and 218, objectively quantify aspects of the operator's physical fitness and performance. The full-body assessment 210 can result in an overall numerical score indicative of an operator's overall physical fitness. The overall numerical score can be composed of scores for the individual components, such as the physician evaluation 212 and various physical capacity assessments 215, 216, 217 and 218. The individual scores can be weighted or not and used to determine the overall physical fitness score.

The occupational assessment 220 can include an occupational capacity assessment 222 that evaluates an operator's ability and/or fitness to perform occupational tasks and fulfill occupational requirements. In order to assess an operator's occupational fitness, the operator can undergo a series of occupational capacity tests 222, such as an occupational strength 223, an occupational endurance 224 and/or an occupational range of motion 225 assessment. The occupational assessments 223, 224 and 225, differ from the physical capacity assessments, 216, 217 and 218, in that they test the operator's physical capacity in performing occupational specific tasks. Upon completion of the occupational assessment 220, the operator can be accorded an overall occupational fitness score, similar to the overall physical fitness score. The occupational fitness score is indicative of the operator's ability and fitness to perform occupational tasks. As with the overall physical fitness score, the overall occupational fitness score can include individual scores for the various occupational assessments an operator undergoes. These scores can be weighted, or otherwise accounted for, in calculating the overall occupational fitness score of an operator.

Further, the overall physical and occupational fitness scores can be used to determine an overall fitness score of the operator. By numerically quantifying the fitness of an operator, metrics and other measurements can be used to determine operator qualification in performing occupational tasks or requirements. The overall fitness score of an operator can include an optional psychological score that can be included in the overall score or alternatively, can influence the physical or occupational fitness score of an operator. Various calculations of the scores, both individual and overall, can be used and the calculations methods can be varied depending on the occupational and/or physical requirements of a selected occupation.

Optionally, the operator can undergo psychological assessment 230 that can include operators, occupational, or other criteria specific psychological assessments designed to assess the psychological state and/or fitness of the operators and their ability to perform future occupational requirements or tasks.

Figure 3:
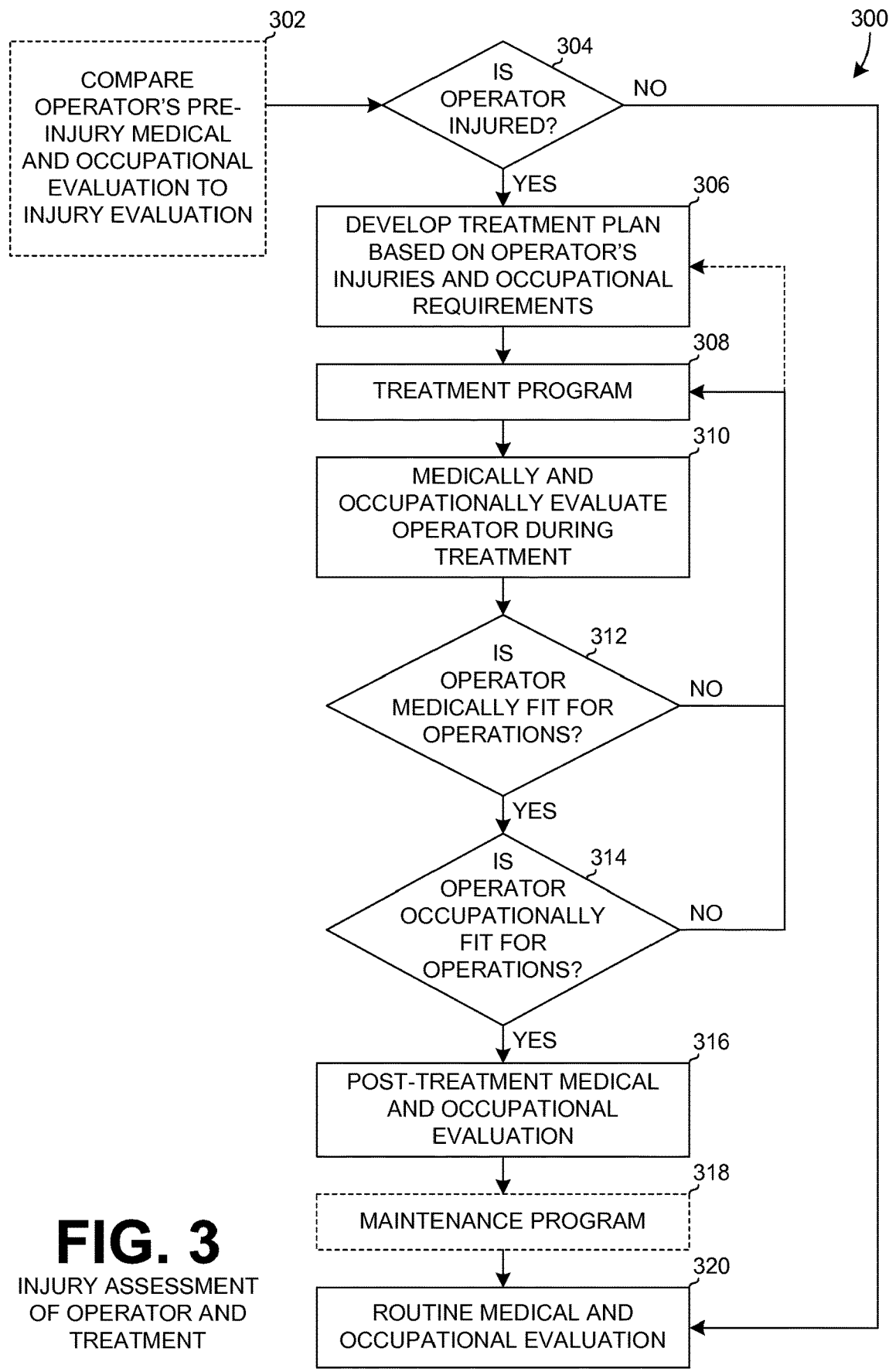
FIG. 3 is an example operator assessment and treatment according to an embodiment of the invention.

FIG. 3 is an example operator assessment and treatment 300 according to an embodiment of the invention. Operator assessment begins with determination of an operator injury 304. The determination can optionally include a comparison between an operator's pre-injury medical and occupational evaluations to those of an injury, or other evaluation, 302 in order to determine if an operator is injured 304. If an operator is determined to be uninjured or injury-free, the operator can continue to undergo routine medical and occupational evaluation 320. These routine evaluation 320 results can be used for comparison 302 to determine the injury status of an operator 304 and can later be used in the operator's injury data that becomes part of the injury trending metrics, described further below.

Referring again to FIG. 3, if it is determined an operator is injured, a treatment plan to repair or rehabilitate the injury 306 is developed. The treatment plan 306 accounts for both the nature of the operator's injury and the occupational requirements expected of the operator when the operator is considered to be fully recovered from the injury.

The operator then undergoes the developed treatment program 308, during which the operator is medically and occupationally evaluated 310 to determine his or her treatment 308 progress. The operator is evaluated 310 to determine his or her medical fitness 312 and occupational fitness 314 for occupational operations and tasks. If the operator is deemed medically and/or occupationally unfit for occupational operations, the operator can continue in the treatment 308 or an alternative treatment plan can be developed 306 based on the medical and occupational evaluations 312 and 314.

Once the operator is deemed both medically and occupationally fit for operations, the operator undergoes a post-treatment medical and occupational evaluation 316. The post-treatment evaluation 316 can establish a new baseline of fitness for the operator and/or establish a post-injury fitness level for the operator.

Optionally, a maintenance program 318 can be developed and executed by the operator in order to maintain the operator's post-treatment fitness level. The maintenance program 318 can be preventative of future injuries of a similar nature or assist the operator in maintaining their fitness, medically and/or occupationally.

The operator then continues to undergo routine medical and occupational evaluations 320 to determine the ongoing physical and occupational fitness of the operator. All or some of the operators, whether previously injured or not, can undergo the routine evaluations 320 so that the physical and occupational fitness of each operator can be tracked versus time and establish an overall group fitness level of the operators.

The Operator Maintenance and Rehabilitation Program

The disclosed methods and systems for rehabilitating an injured operator include developing an evaluation system for evaluating the operator's injuries according to the medical assessment and tactical/occupational assessments discussed above in detail. Optionally, the disclosed methods and systems also can establish a baseline medical and tactical evaluation for the operators before any injury occurs. The optional baseline testing could be performed on the operator near or at the time the operator joins a particular specialized group, like a highly-trained unit such as the Navy Seals or any other SOCOM operator unit. The operators can also be evaluated on a regularly-scheduled or an as-needed/desired basis.

Figure 4:
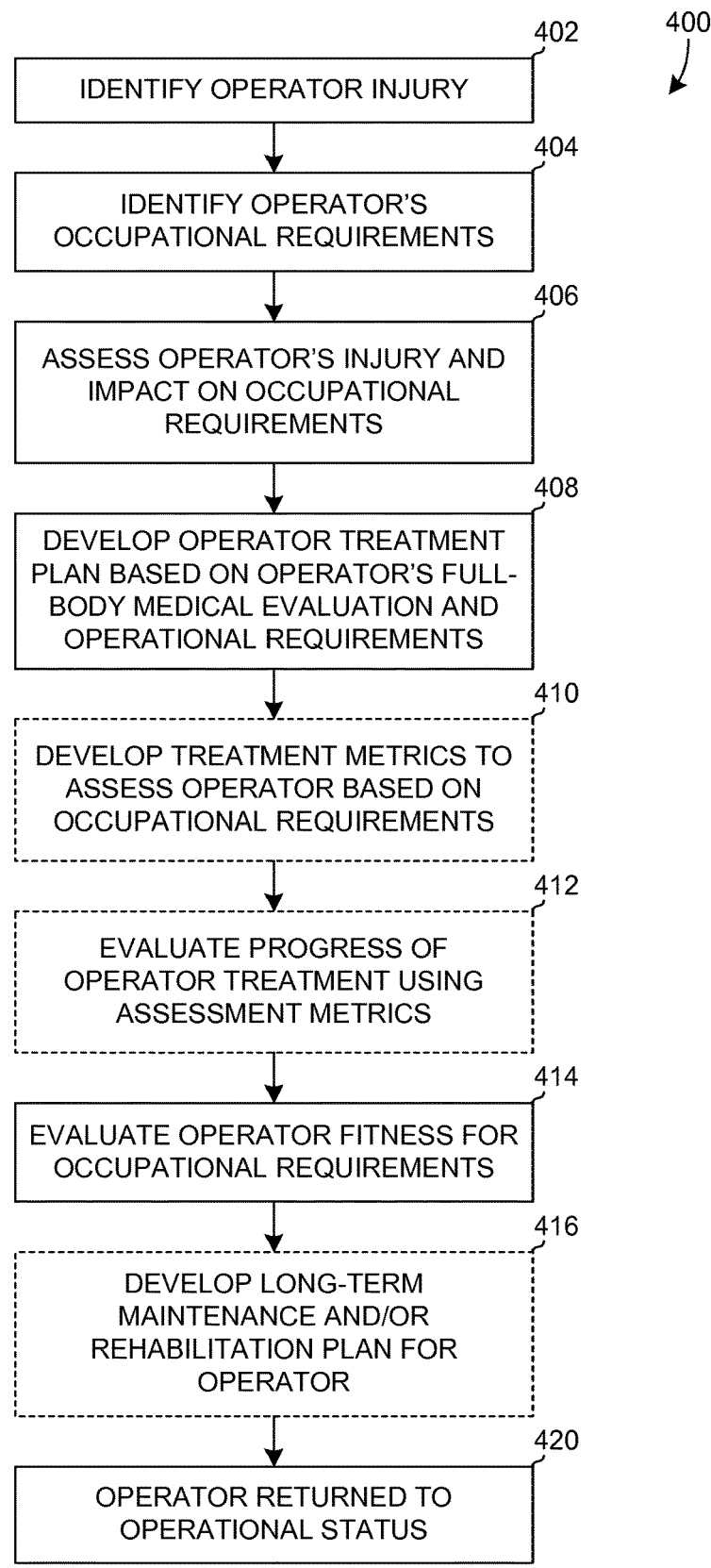
FIG. 4 is an example operator treatment process according to an embodiment of the invention.

FIG. 4 is an example operator treatment process 400 according to an embodiment of the invention. An operator's injury is identified 402 and an operator's occupational requirements are defined or identified 404. An assessment 406 is performed to assess the impact of the operator's injury on the operator's occupational requirements. The assessment highlights the occupational fitness affected by the injury and which aspects of an operator's occupational fitness may need to be focused on during treatment in order for the operator to resume normal occupational duties. During the assessment 406, the operator can be deemed unfit to return to normal occupational duties if the nature or severity of the injury precludes the operator from attaining the necessary occupational fitness required, or desired, to return to normal occupational duties.

A treatment plan 408 for the operator is developed, as shown in FIG. 4. The treatment plan 408 is based on a full-body medical evaluation of the operator and the occupational requirements of the operator's occupation. Optionally, metrics 410 can be established to assess the operator based on the occupational requirements of the operator, which are described further below. The metrics 410 can be used to evaluate 412 the operator's progress through the treatment.

The operator is evaluated for occupational fitness 414 and if deemed fit, is allowed to return to operational status 420. Optionally, a long-term maintenance and/or rehabilitation plan 416 can be developed for the operator to assist in maintaining the operator's fitness level for the operator's occupational requirements.

The disclosed methods and systems for rehabilitating an injured operator can optionally include generating a future plan of care for the injured operator to continue treatment after a desired level of injury recovery is achieved and/or a recommended future physical training plan for improving physical conditioning. Still further, the disclosed methods and systems can also include generating a report for the operator's Commander or other supervisor and tracking and monitoring the operator's injuries. Even further, injuries from multiple operators can optionally be tracked and analyzed. The group injury analysis can be used to treat one or more operators suffering a similar injury to a particular tracked group or can be used to treat one or more operators who are within the same or a similar unit or other group as the tracked group. The Commander's report can also include the injury analysis, both for the individual injured operators and for the units and other groups as a whole.

Specifically, an example program is designed to rehabilitate injured operators back to a combat mission ready status by providing the highest quality medical and tactical evaluation to the operators in the most strategically-efficient methods. Another example program is designed to create a baseline evaluation and future physical training program for the operators known to be at high risk for a chronic, slow on-set type of injury, which can be used in conjunction with the injury treatment programs disclosed herein.

Creating the Operator's Evaluation Plan

Someone can create a customized, injury evaluation plan for an injured operator that includes both a full-body medical assessment and an occupational assessment, such as those discussed in detail above. The operator's evaluation plan is highly-customized to the operator, such as being customized to the operator's occupational requirements, units, mission requirements, injury type, progress of injury, and any other customization characteristics. The operator's evaluation plan can also be customized to injuries the particular operator is likely to suffer based on any criteria like past medical history, past injuries to the same or other body parts, types of missions performed, frequency of missions performed, length of deployments, and any other reason(s).

FIG. 3 shows an example evaluation plan for an injured operator. The evaluation plan's goal is to assess and evaluate previously-injured operators in all aspects of their medical and tactical needs. Further, the results of the evaluation can optionally help a Commander or anyone else in determining whether an operator is ready to return to combat mission ready status or another type of full duty status, needs additional or on-going medical treatment, needs to return to partial duty, and/or cannot return to duty. The results of the operator's evaluation can be used to make any decisions necessary on the medical and tactical conditions of the injured operator.

As shown in FIG. 3, the injured operator first receives a full-body medical assessment that includes a medical physical capacity assessment, a soft tissue treatment and assessment, and an injury assessment, as discussed above. The operator then undergoes tactical evaluations that include assessing the operator's hand-to-hand combat skills, his land-based sky dive skills, his weapons range skill, and his wind tunnel freefall skills. Further, the operator undergoes a PT test and combative physical capacity evaluation along with an open water combat technique swim.

The various medical and tactical evaluations are based on creating the evaluation program for an identified injured operator by first identifying the occupational requirements for the injured operator. The full-body medical evaluation can be designed as a general evaluation or could be tailored to a specific military branch or unit and/or tailored to the specific injury, injury recovery, and/or occupational needs of the injured operator. The operator is evaluated in all areas, both medical and tactical, and then assigned a rating for each. The operator is assigned a medical rating for any one or more of the individual medical evaluations and/or can be assigned an overall medical rating based on the data generated by any one or more of the individual medical evaluations, including all of them.

Further, the operator is assigned a tactical or other occupational rating that is based on the data generated by one, a portion, or all of the tactical or other occupational evaluations. Each of the individual tactical or other occupational evaluations can be assigned an individual tactical or other occupational rating and/or the operator can be assigned an overall tactical or other occupational rating. The overall tactical or other occupation rating can be based on the individual tactical or other occupational ratings of all of the evaluated tactical and other occupational skills. With enough cumulative data, a "go-no go" threshold may be established in order to turn quantitative data into qualitative data.

Optionally, a duty status of the injured operator can be determined based at least in part on the medical rating(s) and the occupational rating(s) for the operator. Frequently, the operator's subjective feedback is also included in the duty status determination, among other considerations. The duty status recommendation can be determined by the evaluation program itself or another entity or person, such as the operator's Commander. For example, the evaluation program itself makes a duty status recommendation for the operator based on the operator's medical and tactical ratings. The evaluation program communicates the operator's medical and tactical ratings along with the operator's recommended duty status to the operator's Commander to make the final decision on whether to return the operator to combat mission ready status or another full or partial duty status.

Creating the Operator's Plan of Care

Optionally, the disclosed methods and systems for rehabilitating an injured operator also include creating a plan of care for the operator. The plan of care can be based on any number of elements, including the operator's assigned medical ratings and tactical or other occupational ratings that are discussed in detail above. Further, the plan of care can also be based on the operator's injury, tactical or other occupational requirements, any one or more of the operator's evaluated medical conditions and/or tactical conditions, etc.

For example, the overall medical rating for an injured operator could be excellent or outstanding, however, the injured operator could be weak in a particular area like having tightness in a particular joint whether the tightness is related to the injury or not. The operator's plan of care includes ongoing treatment or physical therapy to improve the identified weakness even though the operator may be able to either return to duty or needs additional treatment for the injury itself. The program evaluation is designed to improve all aspects of the operator's physical and tactical condition in addition to the injury.

The plan of care can include any treatment, strength and conditioning, physical therapy, procedures, or regular maintenance for the operators. The plan of care can also include a schedule for following up with the operators about their injury status and/or their general medical and tactical skills. The plan of care includes multiple, scheduled follow-up points with the injured operators, and in some examples, the plan of care follow-up with the operators at three months, six months, one year, two years, and five years after the injury or any other suitable follow-up schedule.

Sometimes, the plan of care includes sending the operators an injury evaluation survey. The operators respond to the survey and the evaluation program analyzes the survey results and determines, based on the survey results, whether the operator's plan of care should change, whether additions or adjustments should be made to the plan of care, and if any procedures are recommended and/or additional evaluation is recommended based on the survey responses. The surveys can be sent in addition to or in substitution of one or more follow-up visits with medical providers and can be sent between visits with medical providers to collect between-visit data on the operators' injuries. Sometimes, the operators' leadership may be required to or recommended to supervise the operators in completing the survey or in conducting a test, like a PT activity.

The operator's plan of care can also be communicated to the operator's Commander, in some examples, the operator's unit medical providers, or another person to whom the operator is responsible. Based on the operator's plan of care, the operator's Commander, medical providers, and any other person responsible for the operator's medical care can track the operator's progress through the plan of care and can optionally hold the operator accountable for executing and completing the plan of care. The Operator's medical providers are also given baseline tactical assessment data, if any, to continually assess the Operator's progress with the recommended plan of care.

Figure 5:
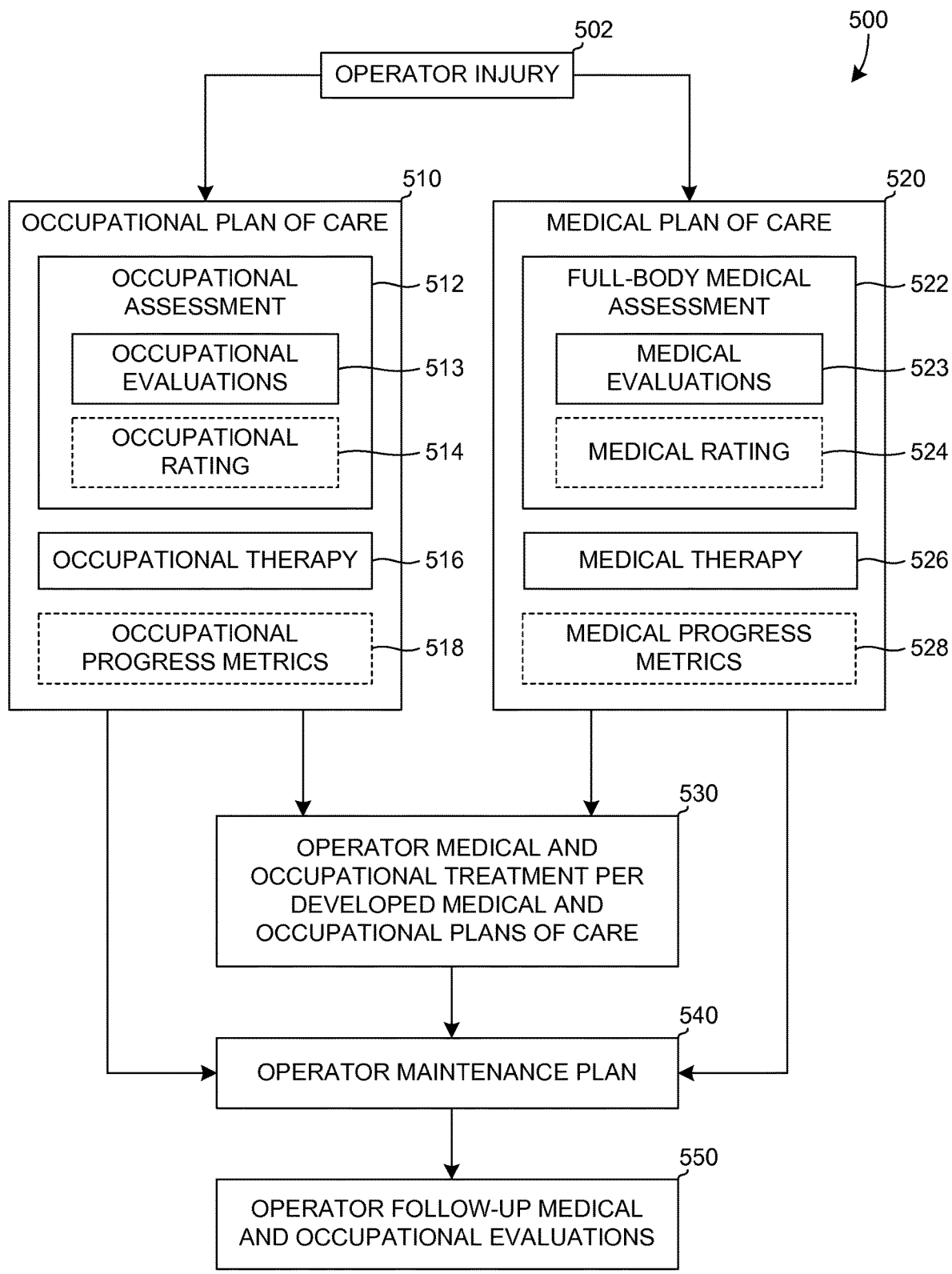
FIG. 5 is an example development of a treatment process according to an embodiment of the invention.

FIG. 5 is an example development of a plan of care and treatment 500 according to an embodiment of the invention. Once an operator is injured 502, a care of plan(s) is developed that, separately or combined, address at least an occupational or a medical fitness aspect of the operator.

An occupational plan of care 510 can be developed for the operator and includes an occupational assessment 510, occupational therapy 516 and, optionally, occupational progress metrics 518. The occupational assessment 512 can include occupational evaluations 513 of the operator and an occupational rating 514 that is associated with the occupational readiness and/or fitness of the operator.

The occupational evaluations 513 can include evaluations of the injured operator's current occupational readiness or fitness and the desired or required level of occupational readiness or fitness required for the operator to return to operations ready status. The occupational rating 514 can include a current occupational rating based on the injured operator's occupational evaluation 513 and a desired or required occupational rating for the operator to achieve before being determined to be occupationally ready.

Occupational therapy 516 can include occupation specific exercises and rehabilitation that an operator can be assigned or expected to execute in order to achieve occupational readiness post-injury. These therapies 516 can be specific to the operator's occupation and occupational requirement and/or can include therapies to assist with the occupational readiness of the operator within a larger operations group. Occupational progress metrics 518 can be developed and employed to measure or track the progress of an operator's treatment as it applies to operations readiness.

A medical plan of care 520 can be developed for the operator and includes a full-body medical assessment 522, medical therapy 526, and optionally, medical progress metrics 528. The full-body medical assessment 522 can include medical evaluations 523 of the operator and a medical rating 524 that is associated with the medical readiness and/or fitness of the operator. The medical evaluations 523 can include evaluations of the injured operator's current medical readiness or fitness and the desired or required level of medical readiness or fitness required for the operator to return to operations ready status. The medical rating 524 can include a current medical rating based on the injured operator's medical evaluation 523 and a desired or required medical rating for the operator to achieve before being determined medically ready.

Medical therapy 526 can include medically specific and general exercises and rehabilitation that an operator can be assigned or expected to execute in order to achieve medical readiness post-injury. These therapies 526 can be specific to the operator's occupation and its medical requirements. Medical progress metrics 528 can be developed and employed to measure or track the progress of an operator's treatment as it applies to operational readiness.

After the occupational 510 and medical 520 plans of care are developed, the operator can undergo both medical and occupational treatments, exercises, and/or rehabilitations 530 per the plans of care 510 and 520. Once the operator has been successfully treated, an operator specific or general maintenance plan 540 can be developed for and/or provided to the operator in order to maintain the operator's occupational and medical fitness. The maintenance plan 540 can act as a treatment plan for some injuries and can also act as a preventative plan to prevent operator injury and/or treat long-term or chronic conditions. The operator is not required to undergo treatment but can instead use a maintenance plan depending on the operator occupation and injury or condition.

The operator can undergo regular or follow-up medical and occupational evaluations 550 to track treatment of the injury or condition and/or the overall medical and occupational fitness of the operator.

Injury Trending Metrics

The disclosed methods and systems for rehabilitating an injured operator can also include an injury trending metrics systems. Such an injury trending metrics systems tracks any one or more element about any number of injured operators across all relevant groups of operators having any one or more common characteristics. The injury trending metrics systems can also analyze and compare compiled operator injury data, which can be used for injury prevention, injury treatment, safety gear evaluations, training evaluations, resources allocated to operators, injury recovery success rates, and other analyses. For example, an injury trending metrics system can include injury information for all operators in SOCOM or any specific branch of the military.

In some examples, the injury trending metrics system tracks all aspects of the medical and occupational and/or tactical evaluations performed on the injured operator. The injury trending metrics system can also track various medical information generated throughout the injury treatment, such as procedures, therapy received, etc. Any of the disclosed injury trending metrics systems can include a database into which the injury information of one or multiple injured operators is stored. The injury tracking system can also include a server and a processor and other computing components, as desired. The server can be a central server to which the injury information is sent for compilation in the injury database. The processor can perform analysis on the received and compiled data. Similar to the military applications, the industrial employer includes any injury data into the injury trending metrics database. The database is dynamic and is continuously changing with additions of new data about new injuries and any analyses performed on the data.

The injury trending metrics can analyze all entered injury data for any one or more injured operators in a variety of ways to determine trends of injuries, types of successful or unsuccessful treatments for particular injuries, likelihood of re-injury based on type of injury or treatment given, timing for injury recoveries, and all other aspects of analyzing the compiled injury data for multiple injured operators. Further, the injury trending metrics can translate costs associated with injuries, such as costs of various medical procedures and/or treatments and costs associated with the operators being unable to perform their duties, into savings for the costs of placing an operator through the disclosed rehabilitation programs.

For example, an operator appears medically ready to return to full combat mission ready status after suffering from a labral tear in his shoulder. The operator was off of full duty for six months and did not perform any tactical, weapons, or physical activities during his time off of duty. After his injury appears to be healed, he could be returned to full combat mission ready duty. If he immediately returns to duty, he is likely to re-injury his shoulder and again be off of duty, could suffer physical pain and need pain medication to mask the pain, he could attempt tactical and/or other occupational requirements and fail, and the like. If the injured operator instead participates in the disclosed rehabilitation programs, the operator is fully medical and tactically evaluated which results in having higher likelihood that his return to full combat mission ready status will be successful or he can receive any necessary further medical treatment and time off of duty to continue allowing his injuries to heal.

The injury trending metrics programs can track the injuries and, for those unable to return to full combat mission ready status, can save time, resources, planning, and money along with improving the safety and well-being of the operator and the operator's colleagues.

The injury trending metrics can also create organized reporting, based on the data generated for all injured operators that can be included in either an individual operator's injury report and/or the individual operator's associated Commander's report and/or in other larger-scale analysis.

For example, an individual injured operator has a typical injury suffered by many other operators within his unit. The individual injured operator's injury information, in the form of an injury report or otherwise, including his medical and tactical or other occupational evaluations, along with his medical records related to the injury and the injury treatment he received are entered into the injury trending metrics system. The injury trending metrics system can provide statistics, analysis, estimates, and the like for the individual operator that are each based on the compiled knowledge of other similarly-situated operators. The similarly-situated operators can be identified by any desired common characteristic between the individual injured operator and the existing data for other injured operators.

The common characteristics include type of injury, age of the injury, injury to same limb or other body part, unit or any other populace, mission requirements, operator age at time of injury, severity of the injury, treatment received, procedures performed, physical therapy completed, origin of injury, whether the injury was suffered during deployment or non-deployment, whether the injury required surgery or other procedures, etc. Further, the common characteristics can be the medical provider or medical facility providing medical treatment to the operator, the treatment plans given to other operators with high injury recovery success rates, and the like. Further, financial analysis of resources devoted to medical treatment for the operators' injuries can be tracked and analyzed. Any common characteristic can be analyzed for the individual injured operator and the individual injured operator's injury data can be compared to any number of other injured operators' data. The injury trending metrics system is dynamic and continuously changing with the addition of new injury data from additional injured operators and from new analyses and comparisons performed on the dynamic data. An injured operator can be analyzed within the injury trending metrics system multiple times, if desired, and from multiple different perspectives.

The injury trending metrics can be performed on any size group of operators from a unit to an entire military branch and beyond. A single operator can have his or her injury data analyzed in the injury trending metrics, which may be particularly useful for an operator who suffers multiple injuries to the same body part or area or to both body parts on opposite sides of his or her body. For example, a SOCOM operator suffers a rotator cuff tear to his left shoulder and later suffers a rotator cuff tear to his right shoulder. The injury data compiled about the operator's first injury to his left rotator cuff can be compared and analyzed with the data about his second rotator cuff tear to his right shoulder. A specialized shoulder-intense physical training program could then be developed for the operator, for example, as a result of the analysis of the operator's injury trending metrics related to both shoulder injuries. Further, the estimated length of time remaining on the operator's career may also be determined based on the shoulder injuries, which can help the operators to plan for the future and for the units and Commanders or other leadership to plan for missions and future allocation of resources.

The injury trending metrics is used to compile data about groups of operators and to analyze the data to generate reports, predictions, future planning, risk assessments, perform financial analysis of resources, safety equipment analyses, and any other useful data. The compiled injury data for each operator is analyzed based on selected criteria and then is transformed into practical, application-specific results. The analysis of the injury data can include performing comparisons, calculations, statistical analyses, and other mathematical relationships or equations using any portion of the injury data. The selected criteria upon which the compiled injury data is analyzed can be any of the above described criteria, like injury type, populace of operator, origin of injury, whether the injury occurred during deployment, whether surgery was recommended or required for the injury, and the like. As discussed above, the selected criteria can also include financial analysis, injury outcome rates, behavior of the operator during the treatment and recovery (e.g., whether the operator completed treatment, missed treatment, failed to participate in treatment, etc.), performance of medical providers and/or facilities, and other aspects of the operator's injury.

The analysis of the injury data based on the selected criteria is what transforms the data. The practical, application-specific results can either be the transformed data or can be some additional application of the transformed data. For example, the transformed data can be an analysis of all SOCOM operators who suffered rotator cuff injuries from discharging their weapons or from hand-to-hand combat during an active combat mission. Those operators' injury types, occupational requirements, tactical training, age of injury from date of onset until date first treated, surgical techniques used to repair the rotator cuff, treatment program, post-surgery physical therapy program, and other data is compiled and compared between and among the SOCOM operators. Trends emerge from analysis of such data, like which surgical techniques and physical therapy programs have the highest success rates and which operators have suffered re-injury. This information may be useful for providing additional training, physical therapy, safety equipment, and the like to the operators and can also be used by Commanders to determine how to best staff future missions and whether the injured operator is likely to be available on a future mission.

In a civilian example, a large industrial employer is likely to have multiple employees who are injured. When an employee is injured on the job, the injury data generated for the injured employee is entered into an injury trending metrics database and optionally into an injury tracking system. An employee's injury report can include information relating to injury statistics for the employee's injury that are based on other employees who suffered similar injuries.

For example, if an employee suffers from a broken arm while performing a machining process at an industrial plant, that employee's injury information can be compared to all other employees who suffered a broken arm while machining. The injured employee's data can be analyzed vis-à-vis the compiled information for other injured employees. Various statistics like average amount of time off of work, average likelihood of full return to job post-injury, etc. can be determined for each injured employee based on the compiled injured employee data.

The employees' injuries can also be tracked and their plan of care can be monitored. For example, an injured employee is given a plan of care to follow, which is input into the tracking system. The employer is then able to follow-up with the employee to determine if the employee is following the plan of care, receiving the recommended treatment, and overall determining if the employee's injury is improving. Based on the employee's tracked plan of care, the employer can hold the employee responsible for performing the necessary injury recommendations to return to work at a full duty or partial duty status.

Further, when the employees are determined to complete their medical treatment, the employers are then able to evaluate the injured employees based on both their medical evaluations and their specific occupational evaluations. The specific occupational evaluations can include any physical action required by the employer of the employee during the employees' performance of their jobs. For example, various physical tests, driving, fine-motor skills, etc. can be evaluated. The employer determines whether to return the employee to work, full or partial duty, based on the combined medical and occupational analysis of the injury evaluation systems, has an estimated view of the employee's path to return to work based on the injury trending metrics system, and has a means of testing the employee before the employee returns to work to increase the likelihood that the employee can successfully and safely perform the required occupational duties.

Figure 6:
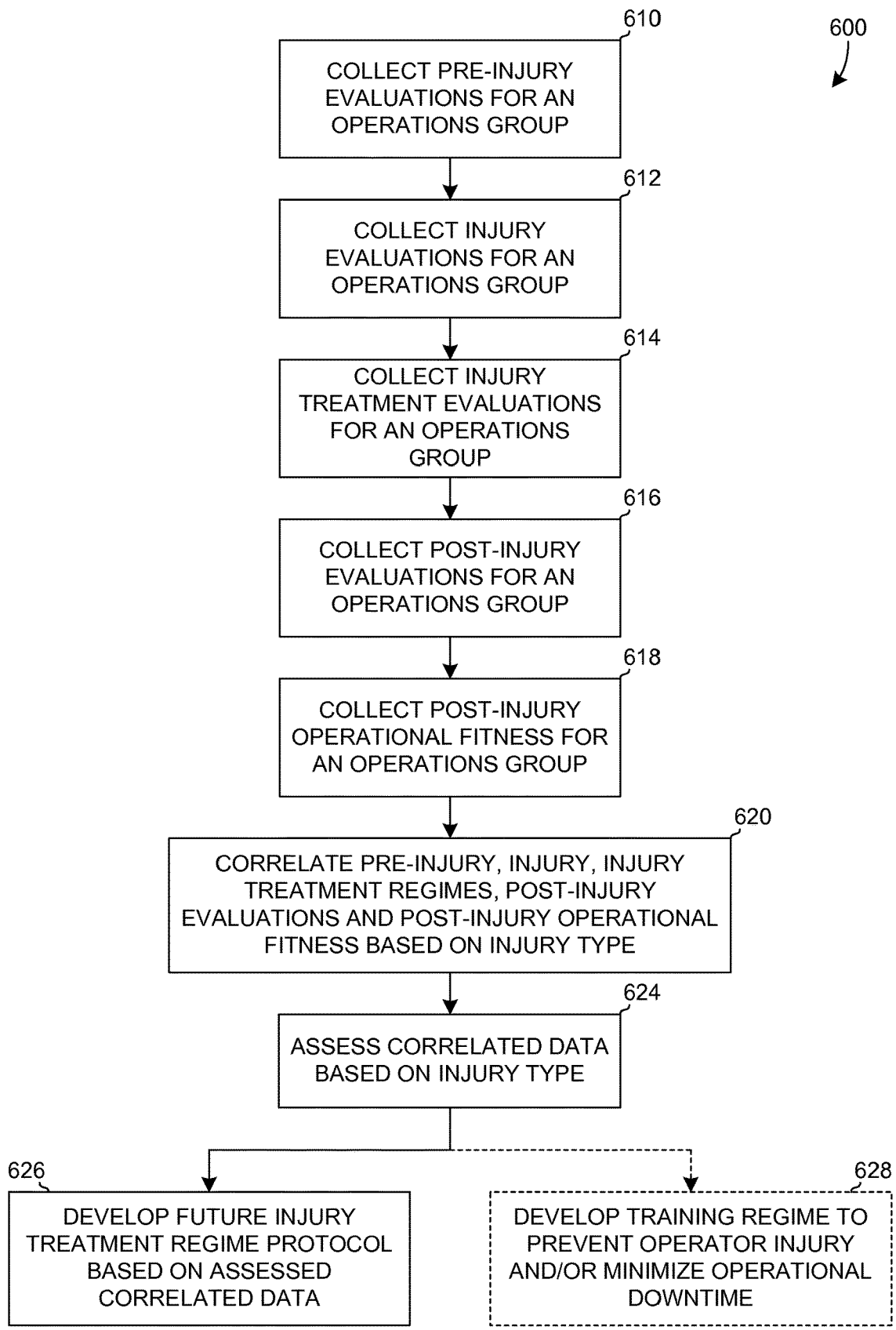
FIG. 6 is an example injury metric process according to an embodiment of the invention.

FIG. 6 is an example injury metric process 600 according to an embodiment of the invention. Pre-injury medical and/or occupational evaluations of an operations group, group of operators, or an operator are collected 610, along with injury evaluations 612, injury treatment evaluations 614, post-injury evaluations 616, and/or post-injury operational fitness 618. The previous evaluations can include medical and/or occupational evaluations for the members of the operations group, the operations group as a whole, a group of operators or an individual operator. The collected evaluations and various other pertinent information of the members of the data collection set are correlated, cross-referenced, and/or otherwise linked or associated 620. The correlated data 620 is then assessed 624 based on injury type or other collected data metric(s). The assessment 624 can be performed in a number of ways including statistical analysis and data analytics. The assessed correlated data can be used to develop future injury treatment protocols 626. The injury protocols 626 can be specific to the injury type, operations group, or other collected data metric. Optionally, preventative training 628, or therapies, can be developed to prevent operator injury and/or minimize operational downtime.

Figure 7:
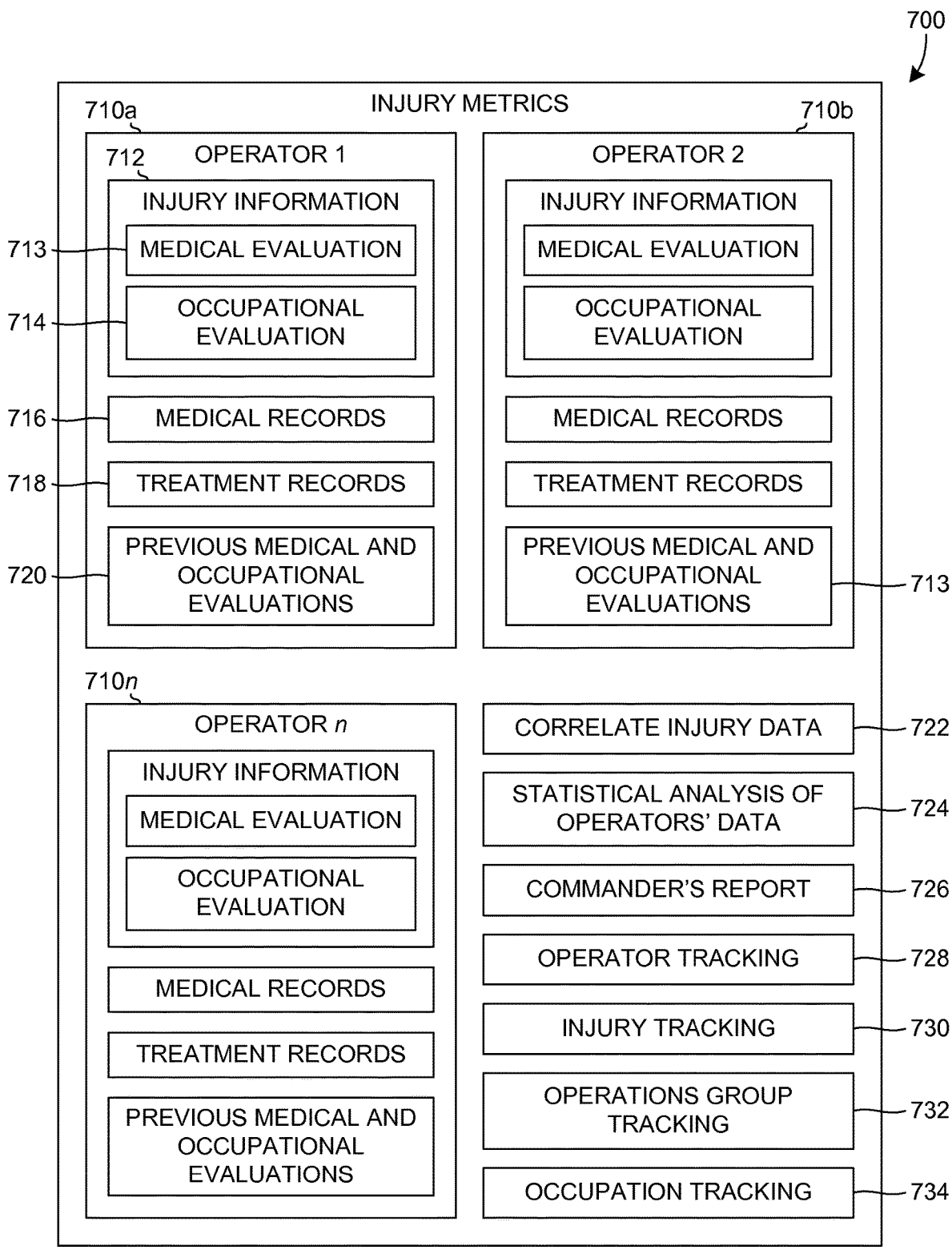
FIG. 7 is an example injury metric system according to an embodiment of the invention.

FIG. 7 is an example injury metric system 700 according to an embodiment of the invention. The system 700 can include any number of operators 710a, 710b . . . 710n and their injury information 712, medical records 716, treatment records 718, and previous medical and occupational evaluations 720. The injury information 712 can include medical 713 and occupational 714 evaluations that were performed on the injured operator 710a, 710b . . . 710n. The injury metric system 700 also includes various reporting and analytic tools, including correlated injury data 722, statistical analysis of operators' data 724, a commander's report 726, operator tracking 728, injury tracking 730, operations group tracking 732 and occupation tracking 734.

Figure 8:
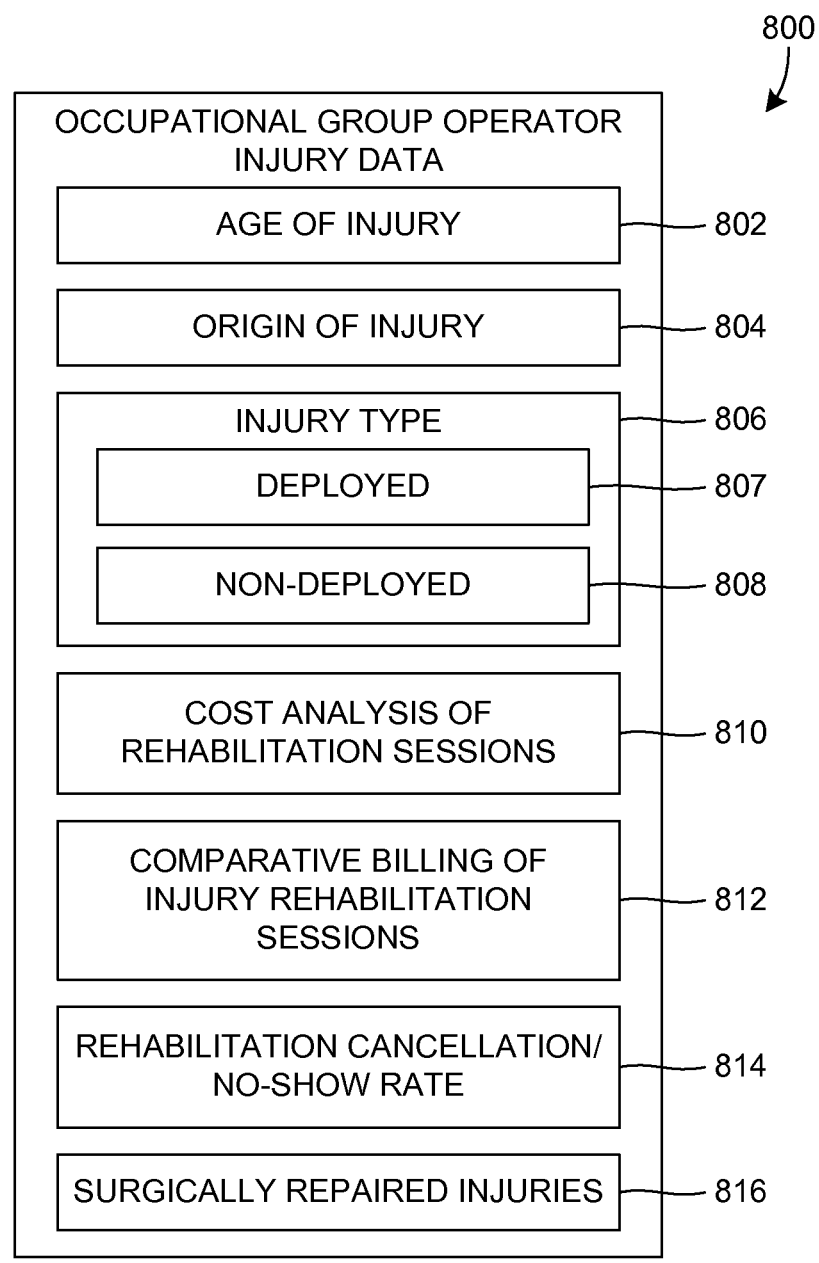
FIG. 8 is example operator injury data that is collected within an example injury metric system according to an embodiment of the invention.

FIG. 8 is example operator injury data 800 that is collected within an example injury metric system according to an embodiment of the invention. The data 800 can include the age of the injury 802, origin of the injury 804, injury type 806, which can include whether injury was received while deployed 807 or not 808, a cost analysis of rehabilitation sessions 810, comparative billing of injury rehabilitation sessions 812, rehabilitation cancellations/no-show rate 814 and data regarding surgically repaired injuries 816.

Injured employees may be tracked slightly differently than injured military operators. For example, an injured employee costs a business both direct costs and indirect costs during the injury treatment period. Sometimes, the injured employees do not return to full work duty status and may go on a light duty status, which is some percentage of their full duty status, or do not return to work. The direct costs that the injured employees cost their employers can include lost wages, medical expenses, and delayed productivity. Indirect costs that the injured employees cost their employers can include both fixed and variable costs such as time to schedule appointments, travel time to appointments, training new employees, overtime pay for employees to cover decreased staff capability, etc. When an employee is injured, both the employee and the employer benefit greatly from high quality treatment of the employee's injury. The employee receives quality injury treatment and the employer receives the benefit of the employee returning to work quickly and fully-recovered.

Employee injury trending metrics can be useful for all aspects of the employee's and employer's needs when an employee injury occurs. For example, the employee's injury information, such as how the injury occurred, what type of injury occurred, the treatment plan, length of time from injury occurrence to treatment initiation, etc. can be compiled. The employee's full-body medical assessment as well as treatment (e g physical rehabilitation) is performed at the time of the injury as well and provides a complete medical picture into the employee's medical condition. The employee's occupational requirements are also assessed. In an injured employee example specifically, the trending injury data is used to identify lost wage data and lost employee productivity data down to an hour-by-hour (or other time period) amount. The trending injury data for employees can also be useful for employers to both understand and track medical expenses, financially plan for future resources that need to be devoted to injured employees both in the work place and as medical expenses. Each injury can be tracked and/or each occupational position can be tracked. Safety policies and equipment can also be evaluated based on this employee injury trending metrics. The cost analysis capacity and translation of work based injuries into financial reporting allows the employer to examine their complete workers' compensation expenses and creates a return on investment (ROI) calculation when the employer utilizes any intervention to reduce these expenses.

The Commander's Report

The disclosed methods and systems for rehabilitating an injured operator can also include a Commander's report. A Commander's report includes any suitable information about the evaluation of the operator, including the operator's medical assessment and tactical or other occupational assessment, the operator's plan of care, if one exists, information about the operator's tracked injury data, and any injury trending metrics analysis performed on either the operator as an individual or the Commander's unit or other injury data.

The operator is evaluated on the medical and tactical bases discussed in detail above. Any portion of the medical and tactical evaluations can be included in the Commander's report including one or more of the specific, isolated medical and/or tactical assessments for the operator. The Commander's report can be customized to the Commander's requests. In some examples, the Commander wants information on the injured operator and all other injured operators suffering a similar injury. The Commander might also want an analysis of the injured operator's injury that includes comparing the injured operator's injury data to data generated from the other injured operators suffering similar injuries. Any of the above-discussed injury trending metrics can be included in the Commander's report and can be made available to the Commander to customize the report.

In another example, the Commander's report includes injury data on all operators currently on injured status in the Commander's unit and/or all plans of care of currently-injured operators in the unit. The Commander's report can include any injury data discussed herein and any desired analysis of that data. The Commander can use the Commander's report to assess the combat mission ready duty status of an injured operator, to assess with operator availability for mission planning, to evaluate unit safety and training procedures, to strategically plan mission based on available operators, or any other assessment required by the Commander.

The Combat Operator Example

An example of the above-described systems and methods is the combat operator system designed for military SOCOM operators who have suffered injuries. The combat operator system provides an injury maintenance system for the highly-trained and highly-valuable operators of SOCOM. The combat operator program combines both the individualized evaluation of the injured operator along with a broad scope of analytic tools, such as the injury trending metrics and/or tracking programs discussed above, for the Commander. The combat operator system is a comprehensive medical evaluation, tactical capacity assessment, trending analytics program created to give SOCOM operators and Commanders a data-driven, safe injury analysis environment.

In this example, program creators design a 3-5 day course over which the injured operator is evaluated simultaneously in both medical and tactical assessments. Typically, the operator selected to participate in the combat operator program has been "off-duty" for a period of four months or more. The medical and tactical data generated in the course provides both the operator and the operator's Commander or other leadership with organized, measured data about the operator's tactical capacity to return to combat mission ready duty status. The course also gives confidence to the operator that he can safely and successfully perform the tactical skills required to complete missions. The operator's course evaluation results in improved, high quality data upon which the Commander or other leadership can make decisions that are based on the injured operator and also results in improved self-confidence in the operator along with improved medical treatment and morale for the operator.

The operators selected for or choosing to participate in the combat operator program have typically completed their plan of care established by their medical team and the medical team has determined that they are fit to return to full combat mission ready duty status. The operator's Commander engages the combat operator program and requests that the operator participate in the program. The combat operator program coordinator with the optional participation of operator's Commander develop a customized program specific to the injured operator being evaluated, which is customized in any of the ways discussed above. The operator completes the combat operator program, including the full-body medical assessment and all tactical assessments, including any optional add-on assessments desired or required by the Commander or other leadership.

The combat operator program generates a plan of care based on the injured operator's medical and tactical assessment from the course. The plan of care is sent to the operator's Commander, Operator's medical team, and is given to the operator. The combat operator program also generates a Commander's report that includes data relating to the injured operator's course evaluation and any other desired data, such as data from the injury trending metrics system. The Commander's report also includes a duty status recommendation for the injured operator based on the combat operator program's evaluation process. The duty status recommendation is a recommendation from the combat operator program coordinators, which might include medical providers, tactical experts, and others, that assesses the injured operator's performance throughout the combat operator program and makes a determination on the operator's duty status.

The operator's duty status is whether the operator is able to perform all of the necessary duties, some of the necessary duties, or none of the necessary duties for his or her occupation. Full combat mission ready duty status means that the operator is cleared to return to full duty and can perform all necessary physical and tactical requirements of the activities associated with his or her occupation. The operator can be required to be on light duty status meaning that the operator can perform some, but not all necessary physical and tactical requirements of the activities associated with his or her occupation. Some operators are unable to return to any duty status based on their performance in the combat operators system in which case the recommendation may be to continue active medical treatment.

Optionally or additionally, a Department of Defense or branch-level report can also be generated related to the injured operator being evaluated, other injured operators with similar characteristics to the evaluated injured operator, and any other requested information.

The Pilot Example

Another example of the above-described systems and methods is the pilot system designed for military pilots and more specifically, fighter jet pilots, like an F-18 pilot, for example. The pilot program is a baseline testing and evaluation program, performed on the fighter pilot's base or installation or sea vessel that generates medical, tactical, and other data about the pilot before the pilot suffers an injury. Pilots are known to suffer slow-onset, chronic injuries to their necks, backs, and spines. The likelihood of a pilot suffering one or more of these kinds of common pilot injuries can be reduced with a customized physical therapy and physical training program. Pilots suffering from common pilot injuries often retire early, suffer with pain, or otherwise have decreased resiliency and/or job performance because of the injuries.

The customized pilot program is created based on baseline evaluations of the pilot before the pilot engages in significant flight missions or trainings that typically generate the common pilot injuries. For example, the pilot is evaluated when the pilot completes flight school and is assigned to a unit in which the pilot is to be actively flying fighter jets. The baseline evaluation can also be done on a SOCOM operator in preparation for any future injuries suffered at which point the SOCOM operator then engages in the combat operator program. Injured pilots can also engage in the combat operator program or any of the other above-described injury evaluation and treatment programs.

Again, the pilot program first conducts a full-body medical and flight-duty specific/occupational/tactical evaluation of a pilot. For example, the pilot's evaluation includes a "McKenzie" based evaluation or other program to evaluate the pilot's medical and occupational conditions. In some examples, the evaluation can include evaluating the pilot on a particular injury strengthening and/or evaluation equipment, such as the MedX™ technology discussed above. The pilot is evaluated on areas that pilots most commonly need strength and conditioning and/or where pilots are most commonly injured including the pilot's lumbar extension isolated isotonic resistance and isometric assessment, torso rotation isolated isotonic resistance, cervical extension isolated isotonic resistance and isometric assessment, and cervical rotation and isolated isotonic resistance along with any one or more of the other full-body medical evaluations discussed above.

The pilot program then develops a customized injury prevention program for the pilot based on the pilot's evaluation. The customized injury prevention program can include a pre-flight physical training, stretching, strengthening, and/or conditioning program for the pilot to perform before each flight. The customized injury prevention program can also include a long program and a short program. The long program can be recommended to the pilot to perform before scheduled flights and the short program can be recommended to the pilot to perform before unexpected or urgent flights.

For example, the pilot's injury prevention program includes injury strengthening and stretching on injury strengthening and/or evaluation equipment that includes range of motion (ROM) work, strength work, endurance of low back extensors, and the like. The pilot is tracked or otherwise monitored during performance of the injury prevention program to make sure that the pilot is performing the activities with the correct mechanics, to monitor the pilot's medical and occupational conditions, and to create accountability with the pilot to engage in the injury prevention program.

Any one or more of the above data generation, injury analysis, injury metrics, tracking systems, reports, or anything else can be embodied in software to help compile, analyze, and manipulate the data in any desired manner.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The invention claimed is:

1. A method of analyzing tending injury data suffered by operators using an operator rehabilitation system, the method comprising:
   at spine evaluation and strengthening equipment of the operator rehabilitation system having a sensor that is structured to be attached to each operator of a plurality of operators:
   measuring evaluation input from the operator in one or more specific aspects of a baseline physical condition of the operator,
   quantifying evaluation data for the one or more specific aspects of the baseline physical condition of the operator, the quantified evaluation data including one or both of range of motion and strength and endurance in one or more positions, and
   generating evaluation output based on one or both of the measured evaluation input and the quantified evaluation data,
   at a display of the operator rehabilitation system: displaying the evaluation output and generating a user prompt to input full-spine medical evaluation data and tactical evaluation data about each operator of the plurality of operators;
   at processing circuitry of the operator rehabilitation system that is electrically coupled to the sensor of the spine evaluation and strengthening equipment for each operator of the plurality of operators:
   receiving the evaluation output from the sensor,
   generating an instruction to display the prompt to the user on the display to input the full-spine medical evaluation data and the tactical evaluation data about the operator, and creating a custom injury prevention program for the operator based on the received evaluation output, the received full-spine medical evaluation data about the operator, and the tactical medical evaluation data about the operator, the custom injury prevention program including one or more of a pre-flight physical training, stretching program, strengthening program and conditioning program, wherein the processing circuitry of the operator rehabilitation system further includes a central server, and at the central server:

receiving at the central server first pre-injury data about a first operator of the plurality of operators, the first pre-injury data including a full-body medical assessment including the full-spine medical evaluation data and a tactical occupational assessment including the tactical medial evaluation data for the first operator before an injury occurs, the first pre-injury data continuously compiled and stored at multiple, regular intervals in a dynamic database;

receiving at the central server a first plan of care for the first operator that includes information related to a first injury suffered by the first operator, the first plan of care including the custom injury prevention program for the first operator and any one or more of multiple treatment elements with a medical provider based at least in part on the tactical occupational assessment of the first operator, the first plan of care continuously compiled and stored in the dynamic database at every one the multiple treatment elements with the medical provider for the first operator;

receiving at the central server second pre-injury data about a second operator of the plurality of operators, the second pre-injury data including a full-body medical assessment including the full-spine medical evaluation data and a tactical occupational assessment including the tactical medial evaluation data for the second operator before an injury occurs, the second pre-injury data continuously compiled and stored a multiple, regular intervals in the dynamic database;

receiving at the central server a second plan of care for the second operator that includes information related to a second injury suffered by the second operator, the second plan of care including the custom injury prevention program for the second operator and any one or more of multiple treatment elements with a medical provider based at least in part on the tactical occupational assessment of the second operator, the second plan of care continuously compiled and stored in the dynamic database at every one of the multiple treatment elements with the medical provider for the second operator;

identifying one or more common characteristics between any one or more of the first pre-injury data, the second pre-injury data, the first operator, the second operator, the first plan of care, and the second plan of care;

analyzing each of the first pre-injury data, the second pre-injury data, the first operator, the second operator, the first plan of care, the second plan of care, and all identified common characteristics between any one or more of the first pre-injury data, the second pre-injury data, the first operator, the second operator, the first plan of care, and the second plan of care to identify one or more trends relating to one or more of the first pre-injury data, the second pre-injury data, the first operator, the second operator, the first plan of care, and the second plan of care;

continuously creating a new dynamic database each time any one of more of the first pre-injury data, the second pre-injury data, the first operator, the second operator, the first plan of care, and the second plan of care is received and each time any one or more trends relating to the first pre-injury data, the second pre-injury data, the first operator, the second operator, the first plan of care, and the second plan of care is identified;

storing each of the continuously created new dynamic databases on the central server; and transforming some portion of the first pre-injury data, the second pre-injury data, the first operator, the second operator, the first plan of care, the second plan of care, and the one or more identified trends into data reflecting whether one or both of the first operator is combat mission ready following the first injury suffered by the first operator and the second operator is combat mission ready following the second injury suffered by the second operator, the first operator being combat mission ready based at least in part on the first pre-injury data and the second operator being combat mission ready based at least in part on the second pre-injury data; and outputting to a user one or more of the identified trends and the transformed data reflecting whether one or both of the first operator following the first injury suffered by the first operator and the second operator following the second injury suffered by the second operator are combat mission ready.

2. The method of claim 1, wherein one or both of the information related to the first injury suffered by the first operator and the information related to the second injury suffered by the second operator includes at least one of a type of injury, age of the injury, injury to same limb or other body part, unit or any other populace, mission requirements, operator age at time of injury, severity of the injury, treatment received, procedures performed, physical therapy completed, origin of injury, whether the injury was suffered during deployment or non-deployment, and whether the injury required surgery or other procedures.

3. The method of claim 1, wherein the tactical occupational assessment for at least one of the first operator and the second operator includes a tactical occupational assessment that is specific to a special operations combat mission to which the at least one of the first operator and the second operator is assigned.

4. The method of claim 1, wherein the first pre-injury data and the second pre-injury data includes both baseline and repeated, maintenance evaluations of the first operator and the second operator, respectively, in both the full-body medical assessment and the tactical occupational assessment.

5. The method of claim 1, wherein the first operator and the second operator are members of the same populace of special operations military operators.

6. The method of claim 1, wherein the first operator and the second operator are members of different populaces of special operations military operators.

7. The method of claim 1, further comprising identifying multiple common characteristics between any one or more of the first pre-injury data, the second pre-injury data, the first operator, the second operator, the first plan of care, and the second plan or care.

8. The method of claim 1, in response to receiving the first plan of care, generating comparative data between the first pre-injury data and the first plan of care and storing the comparative data in the dynamic database.

9. The method of claim 1, further comprising generating a report that includes at least in part on the identified one or more common characteristics and the identified trends, storing the generated report on the central server, and outputting the generated report from the central server.

10. The method of claim 1, wherein the first pre-injury data includes objective results from performance based metrics of the first operator and the second pre-injury data includes objective results from performance based metrics of the second operator.

11. The method of claim 1, further comprising identifying one or more tactical activities known to be more difficult for an operator suffering from the identified first injury based at least in part of the first pre-injury data and developing a tactical evaluation that identifies tactical activities to specifically customize the first plan of care based on the identified trends relating to the first operator, the first pre-injury data, the first plan of care, and including the identified one or more tactical activities.

12. An injury trending metrics system, comprising:
an operator rehabilitation system, including:
spine evaluation and strengthening equipment having a sensor that is structured to be attached to each operator of a plurality of operators and is configured to:
measure evaluation input from the operator in one or more specific aspects of a baseline physical condition of the operator;
quantify evaluation data for the one or more specific aspects of the baseline physical condition of the operator, the quantified evaluation data including one or both of range of motion and strength and endurance in one or more positions;
generate evaluation output based on one or both of the measured evaluation input and the quantified evaluation data;
a display that is configured to display the output and to generate a user prompt to input full-spine medical evaluation data about the operator and tactical evaluation about the operator;
processing circuitry electrically coupled to the sensor of the spine evaluation and strengthening equipment, the processing circuitry configured to:
receive the evaluation output from the sensor;
generate an instruction to display the prompt to the user on the display to input the full-spine medical evaluation data and the tactical evaluation about the operator;
create a custom injury prevention program for the operator based on the received evaluation output, the received full-spine medical evaluation data about the operator, and the tactical medical evaluation about the operator, the custom injury prevention program including one or more of a pre-flight physical training, stretching program, strengthening program and conditioning program; and
a central server configured to:
receive first pre-injury data about a first operator of the plurality of operators, the first pre-injury data including a full-body medical assessment including the full-spine medical evaluation data and a tactical occupational assessment including the tactical medial evaluation data for the first operator before an injury occurs, the first pre-injury data continuously compiled and stored at multiple, regular intervals in a dynamic database stored on the central server;
receive a first plan of care for the first operator that includes information related to a first injury suffered by the first operator, the first plan of care including the custom injury prevention program for the first operator and any one or more multiple treatment elements with a medical provider based at least in part on the tactical occupational assessment of the first operator, the first plan of care continuously compiled and stored in the dynamic database at every one of the multiple treatment elements with the medical provider for the first operator;
receive second pre-injury data about a second operator of the plurality of operators, the second pre-injury data including a full-body medical assessment including the full-spine medical evaluation data and a tactical occupational assessment including the tactical medial evaluation data for the second operator before an injury occurs, the second pre-injury data continuously compiled and stored at multiple, regular intervals in the dynamic database;
receive a second plan of care for the second operator that includes information related to a second injury suffered by the second operator, the second plan of care including the custom injury prevention program for the second operator and any one or more multiple treatment elements with a medical provider based at least in part on the tactical occupational assessment of the second operator, the second plan of care continuously compiled and stored in the dynamic database at every one of the multiple treatment elements with the medical provider for the second operator; and
a processor electrically coupled to the central server and configured to:
identify one or more common characteristics between any one or more of the first pre-injury data, the second pre-injury data, the first operator, the second operator, the first plan of care, and the second plan of care;
analyze each of the first pre-injury data, second pre-injury data, the first operator, the second operator, the first plan of care, and the second plan of care, and all identified common characteristics between any one or more of the first pre-injury data, the second pre-injury data, the first operator, the second operator, the first plan of care, and the second plan of care to identify one or more trends related to one or more of the first pre-injury data, the second pre-injury data, the first operator, the second operator, the first plan of care, and the second plan of care;
continuously create a new dynamic database each time any one or more of the first pre-injury data, the second pre-injury data, the first operator, the second operator, the first plan of care, and the second plan of care is received and each time any one or more trends relating to the first pre-injury data, the second pre-injury data, the first operator, the second operator, the first plan of care, and the second plan of care is identified;
cause the new dynamic database to be stored on the central server after each time the new dynamic database is created;

transform some portion of the first pre-injury data, the second pre-injury data, the first operator, the second operator, the first plan of care, the second plan of care, and the one or more identified trends into data reflecting whether one or both of the first operator is combat mission ready following the first injury suffered by the first operator based at least in part on the pre-injury data and the second operator is combat mission ready following the second injury suffered by the second operator based at least in part on the pre-injury data of the second operator; and output one or more of the identified trends and the transformed data reflecting whether one or both of the first operator following the first injury suffered by the first operator and the second operator following the second injury suffered by the second operator are combat mission ready.

13. The injury trending metrics system of claim 12, wherein each operator of the plurality of operators is a pilot and the baseline physical condition is based on one or more selected from multiple of common pilot spine injuries.

14. The injury trending metrics system of claim 12, wherein the sensor is further configured to:

measure post-injury spine evaluation input from the operator in one or more specific aspects of a post-injury physical condition of the operator;

quantify post-injury spine evaluation data for the one or more specific aspects of the post-injury spine physical condition of the operator, the post-injury evaluation data including one, multiple, or any combination of: range of motion and strength and endurance in one or more positions; and generate post-injury spine evaluation output that includes one or both of the quantified post-injury evaluation input and the quantified post-injury spine evaluation data.

15. The injury trending metrics system of claim 14, wherein the processing circuitry is further configured to receive the post-injury evaluation output and to create a customized post-injury spine plan of care based at least in part on one of or any combination of the full spine medical evaluation data, the tactical evaluation, and the post-injury spine evaluation output.

16. The injury trending metrics system of claim 14, wherein the post-injury spine evaluation input includes one or both of a symptomatic injury and an asymptomatic anatomical spine injury.

17. The injury trending metrics system of claim 14, wherein the post-injury spine evaluation input includes input about a single injury or multiple injuries.

18. The injury trending metrics system of claim 12, wherein the spine evaluation and strengthening equipment is configured to:

measure injury spine evaluation data of the operator in one or more specific aspects of a post-injury physical condition spine injury of the operator;

quantify spine injury evaluation data for the one or more specific aspects of the post-injury physical condition of the operator including one or more of: range of motion and strength and endurance in one or more positions; and generate spine injury evaluation output that includes one or both of the measured spine injury evaluation data and the quantified injury spine evaluation data.

19. An injury trending metrics system, comprising:
an operator rehabilitation system, including:

spine evaluation and strengthening equipment having a sensor that is structured to be attached to each operator of a plurality of operators and is configured to:

measure evaluation input from the operator in one or more specific aspects of a baseline physical condition of the operator;

quantify evaluation data for the one or more specific aspects of the baseline physical condition of the operator, the quantified evaluation data including one or both of range of motion and strength and endurance in one or more positions;

generate evaluation output based on one or both of the measured evaluation input and the quantified evaluation data;

a display that is configured to display the output and to generate a user prompt to input full-spine medical evaluation data about the operator and tactical evaluation about the operator;

processing circuitry electrically coupled to the sensor of the spine evaluation and strengthening equipment, the processing circuitry configured to:

receive the evaluation output from the sensor;

generate an instruction to display the prompt to the user on the display to input the full-spine medical evaluation data and the tactical evaluation about the operator;

create a custom injury prevention program for the operator based on the received evaluation output, the received full-spine medical evaluation data about the operator, and the tactical medical evaluation about the operator, the custom injury prevention program including one or more of a pre-flight physical training, stretching program, strengthening program and conditioning program; and means for receiving at a central server first pre-injury data about a first operator of the plurality of operators, the first pre-injury data including a full-body medical assessment including the full-spine medical evaluation data and a tactical occupational assessment including the tactical medial evaluation data for the first operator before an injury occurs, the first pre-injury data continuously compiled and stored at multiple, regular intervals in a dynamic database;

means for receiving at the central server a first plan of care for the first operator that includes information related to a first injury suffered by the first operator, the first plan of care including the custom injury prevention program for the first operator and any one or more of multiple treatment elements with a medical provider based at least in part on the tactical occupational assessment of the first operator, the first plan of care continuously compiled and stored in the dynamic database at every one of the multiple treatment elements with the medical provider for the first operator;

means for receiving at the central server second pre-injury data about a second operator of the plurality of operators, the second pre-injury data including a full-body medical assessment including the full-spine medical evaluation data and a tactical occupational assessment including the tactical medial evaluation data for the second operator before an injury occurs, the second pre-injury data continuously compiled and stored at multiple, regular intervals in the dynamic database;

means for receiving at the central server a second plan of care for the second operator that includes information related to a second injury suffered by the second operator, the second plan of care including the custom injury prevention program for the second operator and any one or more of multiple treatment elements with a medical provider based at least in part on the tactical occupational assessment of the second operator, the second plan of care continuously compiled and stored in the dynamic databased at every on of the multiple treatment elements with the medical provider for the second operator;

means for identifying one or more common characteristics between any one or more of the first pre-injury data, the second pre-injury data, the first operator, the second operator, the first plan of care, and the second plan of care;

means for analyzing each of the first pre-injury data, the second pre-injury data, the first operator, the second operator, the first plan of care, the second plan of care, and all identified common characteristics between any one or more of the first pre-injury data, the second pre-injury data, the first operator, the second operator, the first plan of care, and the second plan of care to identify one or more trends relating to one or more of the first pre-injury data, the second pre-injury data, the first operator, the second operator, the first plan of care, and the second plan of care;

means for continuously creating a new dynamic database each time any one or more of the first pre-injury data, the second pre-injury data, the first operator, the second operator, the first plan of care, and the second plan of care is received and each time any one or more trends relating to the first pre-injury data, the second pre-injury data, the first operator, the second operator, the first plan of care, and the second plan of care is identified;

means for storing each of the continuously created new dynamic databases on the central server;

means for transforming some portion of the first pre-injury data, the second pre-injury data, the first operator, the second operator, the first plan of care, the second plan of care, and the one or more identified trends into data reflecting whether one of both of the first operator is combat mission ready following the first injury suffered by the first operator and the second operator is combat mission ready following the second injury suffered by the second operator, the first operator being combat mission ready based at least in part on the first pre-injury data and the second operator being combat mission ready based at least in part on the second pre-injury data; and means for outputting to a user one or more of the identified trends and the transformed data reflecting whether one or both of the first operator following the first injury suffered by the first operator and the second operator following the second injury suffered by the second operator are combat mission ready.

* * * * *